(12) United States Patent
Harris et al.

(10) Patent No.: US 9,050,427 B2
(45) Date of Patent: Jun. 9, 2015

(54) DRY POWDER INHALERS WITH MULTI-FACET SURFACE DEAGGLOMERATION CHAMBERS AND RELATED DEVICES AND METHODS

(75) Inventors: David Harris, Milton (GB); George McGee Perkins, Histon (GB); John Kenneth Hainsworth, Rawdon (GB); Charles A. Buckner, III, Chapel Hill, NC (US)

(73) Assignee: Oriel Therapeutics, Inc., Durham, NC (US)

( * ) Notice: Subject to any disclaimer, the term of this patent is extended or adjusted under 35 U.S.C. 154(b) by 769 days.

(21) Appl. No.: 13/054,808

(22) PCT Filed: Sep. 25, 2009

(86) PCT No.: PCT/US2009/005336
§ 371 (c)(1),
(2), (4) Date: Mar. 9, 2011

(87) PCT Pub. No.: WO2010/039201
PCT Pub. Date: Apr. 8, 2010

(65) Prior Publication Data
US 2011/0174306 A1 Jul. 21, 2011

Related U.S. Application Data

(60) Provisional application No. 61/101,175, filed on Sep. 30, 2008.

(51) Int. Cl.
*A61M 15/00* (2006.01)
*B05D 7/14* (2006.01)
*B65D 83/06* (2006.01)

(52) U.S. Cl.
CPC ....... *A61M 15/0045* (2013.01); *A61M 15/0035* (2014.02); *A61M 15/0051* (2014.02)

(58) Field of Classification Search
USPC ............................ 128/13, 14, 15, 19, 21, 23, 128/203.12–203.15, 203, 203.21, 203.23
See application file for complete search history.

(56) References Cited

U.S. PATENT DOCUMENTS

| 4,627,432 A | 12/1986 | Newell et al. |
| 4,778,054 A | 10/1988 | Newell et al. |

(Continued)

FOREIGN PATENT DOCUMENTS

| DE | 19500764 | 7/1996 |
| EP | 1106196 | 3/2001 |

(Continued)

OTHER PUBLICATIONS

Hickey et al., A new millennium for inhaler technology, 21 Pharm. Tech., n. 6, pp. 116-125 (1997).

(Continued)

*Primary Examiner* — Tan-Uyen (Jackie) T Ho
*Assistant Examiner* — Mark Wardas
(74) *Attorney, Agent, or Firm* — Myers Bigel Sibley & Sajovec

(57) ABSTRACT

Dry powder inhalers and methods are provided that facilitate deagglomeration of powdered medicament during inspiration. A dry powder inhaler includes a dry powder medicament container assembly, and an elongated dry powder delivery tube having an inlet at one end that communicates with a dose container, and an outlet or inhalation port that extends from the inhaler housing at an opposite end. The delivery tube includes one or more apertures adjacent the inlet that cause cyclonic or turbulent airflow through the delivery tube. The inner surface of the delivery tube has a polygonal configuration and the cyclonic air stream bounces off the polygonal inner surface numerous times as the air stream flows through the delivery tube. Another dry powder inhaler includes a deagglomeration chamber with a polygonal inner surface. An air stream containing dry powder medicament is directed into the deagglomeration chamber and impacts the polygonal inner surface numerous times.

15 Claims, 15 Drawing Sheets

(56) References Cited

U.S. PATENT DOCUMENTS

| | | | |
|---|---|---|---|
| 4,811,731 A | 3/1989 | Newell et al. | |
| 5,035,237 A | 7/1991 | Newell et al. | |
| 5,138,138 A | 8/1992 | Theilacker et al. | |
| 5,327,883 A | 7/1994 | Williams et al. | |
| 5,337,740 A | 8/1994 | Armstrong et al. | |
| 5,388,572 A | 2/1995 | Mulhauser et al. | |
| 5,529,059 A | 6/1996 | Armstrong et al. | |
| 5,533,502 A | 7/1996 | Piper | |
| 5,590,645 A | 1/1997 | Davies et al. | |
| 5,622,166 A | 4/1997 | Eisele et al. | |
| 5,715,810 A | 2/1998 | Armstrong et al. | |
| 5,727,607 A | 3/1998 | Ichikawa et al. | |
| 5,769,073 A | 6/1998 | Eason et al. | |
| 5,857,457 A * | 1/1999 | Hyppola | 128/203.15 |
| 5,860,419 A | 1/1999 | Davies et al. | |
| 5,873,360 A | 2/1999 | Davies et al. | |
| 5,909,829 A | 6/1999 | Wegman et al. | |
| 5,921,237 A | 7/1999 | Eisele et al. | |
| 5,947,169 A | 9/1999 | Wegman et al. | |
| 6,029,663 A | 2/2000 | Eisele et al. | |
| 6,032,666 A | 3/2000 | Davies et al. | |
| 6,082,356 A | 7/2000 | Stradella | |
| 6,116,238 A | 9/2000 | Jackson et al. | |
| 6,245,339 B1 | 6/2001 | Van Oort et al. | |
| 6,328,033 B1 | 12/2001 | Avrahami | |
| 6,367,473 B1 | 4/2002 | Käfer | |
| 6,378,519 B1 | 4/2002 | Davies et al. | |
| 6,445,941 B1 | 9/2002 | Hampton et al. | |
| 6,536,427 B2 | 3/2003 | Davies et al. | |
| 6,543,448 B1 | 4/2003 | Smith et al. | |
| 6,550,477 B1 | 4/2003 | Casper et al. | |
| 6,591,832 B1 | 7/2003 | DeJonge | |
| 6,655,381 B2 | 12/2003 | Keane et al. | |
| 6,668,827 B2 | 12/2003 | Schuler et al. | |
| 6,679,254 B1 | 1/2004 | Rand et al. | |
| 6,792,945 B2 | 9/2004 | Davies et al. | |
| 6,810,872 B1 | 11/2004 | Ohki et al. | |
| 6,871,647 B2 | 3/2005 | Allan et al. | |
| 6,880,555 B1 | 4/2005 | Brunnberg et al. | |
| 6,915,802 B1 | 7/2005 | Anderson et al. | |
| 6,923,178 B2 | 8/2005 | Snow | |
| 6,948,494 B1 | 9/2005 | Snow | |
| 7,089,935 B1 | 8/2006 | Rand | |
| 7,219,665 B1 | 5/2007 | Braithwaite | |
| 7,225,808 B2 | 6/2007 | Davies et al. | |
| 7,275,538 B2 | 10/2007 | Nakamura et al. | |
| 7,318,436 B2 | 1/2008 | Snow | |
| 7,389,775 B2 | 6/2008 | Davies et al. | |
| 7,503,324 B2 | 3/2009 | Barney et al. | |
| 7,571,723 B2 | 8/2009 | Braithwaite | |
| 7,571,724 B2 | 8/2009 | Braithwaite | |
| 8,443,798 B2 | 5/2013 | Eason et al. | |
| 8,511,304 B2 | 8/2013 | Anderson et al. | |
| 2001/0007853 A1 | 7/2001 | Dimarchi et al. | |
| 2001/0053761 A1 | 12/2001 | Dimarchi et al. | |
| 2002/0040713 A1 | 4/2002 | Eisele et al. | |
| 2002/0170560 A1 | 11/2002 | Young et al. | |
| 2003/0178024 A1 | 9/2003 | Allan et al. | |
| 2004/0025877 A1 | 2/2004 | Crowder et al. | |
| 2005/0056281 A1 | 3/2005 | Snow | |
| 2005/0126568 A1 | 6/2005 | Davies et al. | |
| 2005/0154491 A1 | 7/2005 | Anderson et al. | |
| 2005/0161041 A1 | 7/2005 | Schuler et al. | |
| 2005/0172963 A1 | 8/2005 | Allan et al. | |
| 2006/0102511 A1 | 5/2006 | Pasbrig et al. | |
| 2006/0157053 A1 | 7/2006 | Barney et al. | |
| 2007/0062525 A1 | 3/2007 | Bonney et al. | |
| 2007/0131225 A1 | 6/2007 | Rand | |
| 2007/0137643 A1 | 6/2007 | Bonney et al. | |
| 2007/0137645 A1 | 6/2007 | Eason et al. | |
| 2007/0181123 A1 | 8/2007 | Houzego | |
| 2007/0181124 A1 | 8/2007 | Casper et al. | |
| 2007/0215149 A1 | 9/2007 | King et al. | |
| 2007/0221218 A1 | 9/2007 | Warden et al. | |
| 2007/0235029 A1 | 10/2007 | Zhu et al. | |
| 2008/0127971 A1 | 6/2008 | King et al. | |
| 2008/0223366 A1 | 9/2008 | Davies et al. | |
| 2009/0013994 A1 * | 1/2009 | Jones et al. | 128/200.23 |
| 2009/0114220 A1 | 5/2009 | Wachtel et al. | |
| 2010/0197565 A1 * | 8/2010 | Smutney et al. | 514/3 |
| 2011/0094507 A1 | 4/2011 | Wachtel et al. | |
| 2013/0032144 A1 | 2/2013 | Miller et al. | |

FOREIGN PATENT DOCUMENTS

| | | |
|---|---|---|
| EP | 1 779 884 A1 | 5/2007 |
| EP | 1844805 | 10/2007 |
| GB | 873410 | 7/1961 |
| GB | 2340758 | 3/2000 |
| WO | WO 94/14490 | 7/1994 |
| WO | WO 94/20164 | 9/1994 |
| WO | WO 98/41265 | 9/1998 |
| WO | WO 99/36116 | 7/1999 |
| WO | WO 00/45879 | 8/2000 |
| WO | WO 01/28616 | 4/2001 |
| WO | WO 01/34234 | 5/2001 |
| WO | WO 02/053215 | 7/2002 |
| WO | WO 02/053216 | 7/2002 |
| WO | WO 03/011708 | 2/2003 |
| WO | WO 2004/045487 | 6/2004 |
| WO | WO 2004/045487 A2 | 6/2004 |
| WO | WO 2005/002654 | 1/2005 |
| WO | WO 2005/037353 | 4/2005 |
| WO | WO 2005/044173 | 5/2005 |
| WO | WO 2005/110519 | 11/2005 |
| WO | WO 2006/031775 | 3/2006 |
| WO | WO 2006/108877 | 10/2006 |
| WO | WO 2007/007110 | 1/2007 |
| WO | WO 2007/012871 | 2/2007 |
| WO | WO 2008/039182 A1 | 4/2008 |

OTHER PUBLICATIONS

International Search Report and Written Opinion for corresponding PCT application No. PCT/US2009/058285, date of mailing Apr. 14, 2010.

Notification of Transmittal of the International Search Report and the Written Opinion of the International Searching Authority issued May 14, 2010 by the Korean Intellectual Property Office for PCT Application No. PCT/US2009/005338.

Notification of Transmittal of the International Search Report and the Written Opinion of the International Searching Authority, or the Declaration issued by the European Patent Office on Jan. 7, 2010 for the corresponding International Application No. PCT/US2009/058281.

PCT International Search Report and Written Opinion for PCT Application No. PCT/US2009/058281, Date of Mailing Jan. 7, 2010.

PCT Invitation to Pay Additional Fees and Partial Search for corresponding PCT Application No. PCT/US2009/058285, Date of Mailing Dec. 30, 2009.

Prime et al., Review of Dry Powder Inhalers, 26 Adv. Drug Delivery Rev., pp. 51-58 (1997).

Wolff et al., Generation of Aerosolized Drugs, J. Aerosol. Med., pp. 88-106 (1994).

Notification of Transmittal of the International Search Report and the Written Opinion of the International Searching Authority issued May 4, 2010 by the Korean Intellectual Property Office for corresponding PCT Application No. PCT/US20098/005336.

* cited by examiner

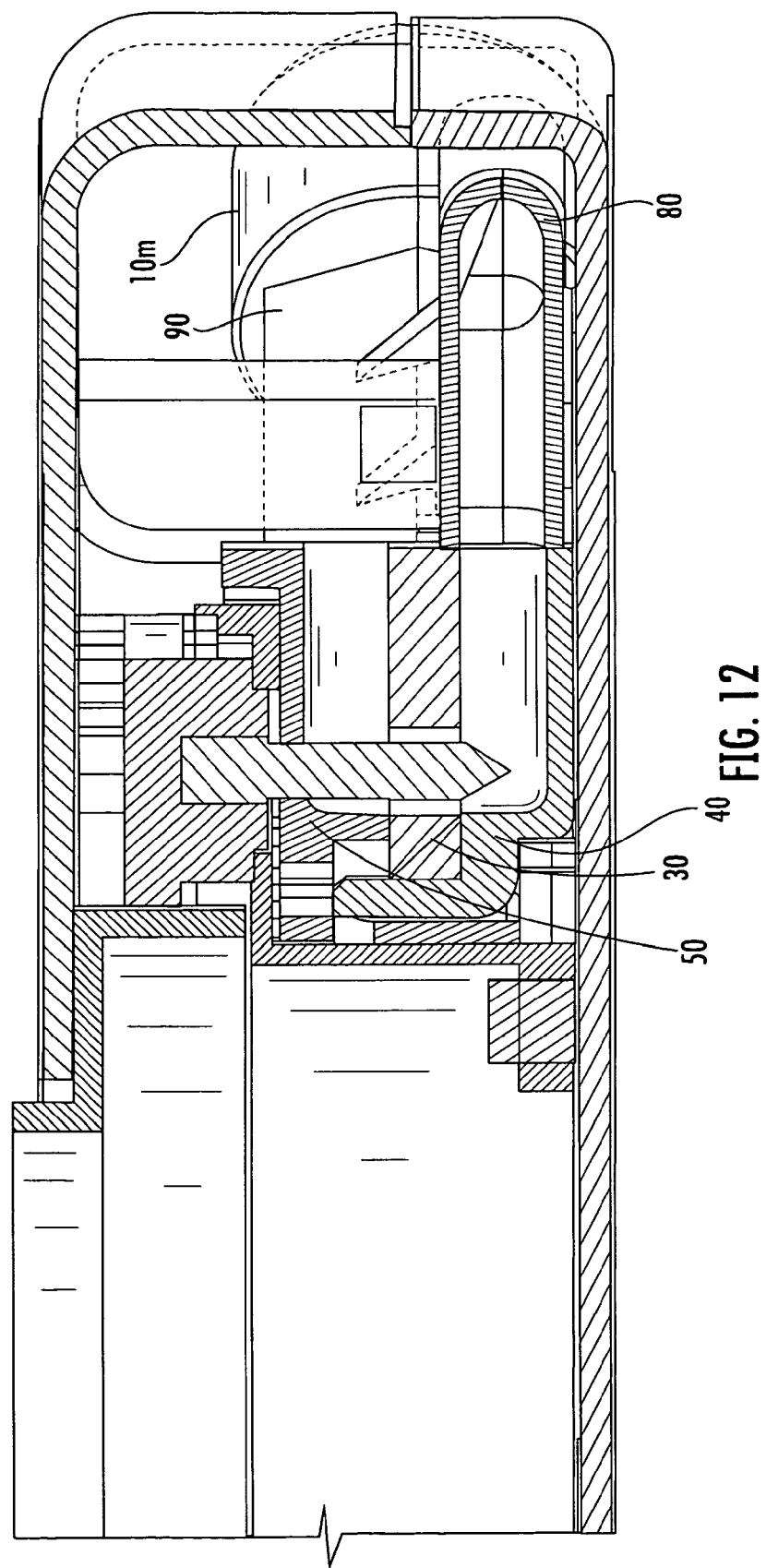

```
┌─────────────────────┐
│ ENTRAIN DRY POWDER  │
│ MEDICAMENT WITHIN AIR│──100
│       STREAM        │
└──────────┬──────────┘
           │
           ▼
┌─────────────────────┐
│ DIRECT AIR STREAM AGAINST│
│ POLYGONAL INNER SURFACE OF│
│ DELIVERY CONDUIT/TUBE,│──110
│ RESULTING IN MULTIPLE│
│ IMPACTS AND SWIRLING AIRFLOW│
└─────────────────────┘
```

FIG. 17

DRY POWDER INHALERS WITH MULTI-FACET SURFACE DEAGGLOMERATION CHAMBERS AND RELATED DEVICES AND METHODS

RELATED APPLICATIONS

This application is a 35 USC 371 national phase application of PCT/US 2009/005336, filed Sep. 25, 2009, which claims the benefit of and priority to U.S. Provisional Application Ser. No. 61/101,175, filed Sep. 30, 2008, the contents of which are hereby incorporated by reference as if recited in full herein.

FIELD OF THE INVENTION

The present invention relates to inhalers, and may be particularly suitable for dry powder inhalers.

BACKGROUND

Dry powder inhalers (DPIs) are an alternative to pMDI (pressurized meted dose inhaler) devices for delivering drug aerosols without using propellants. Typically, DPIs are configured to deliver a powdered drug or drug mixture that includes an excipient and/or other ingredients. Generally described, known single and multiple dose dry powder DPI devices use: (a) individual pre-measured doses in blisters containing the drug, which can be inserted into the device prior to dispensing; or (b) bulk powder reservoirs which are configured to administer successive quantities of the drug to the patient via a dispensing chamber which dispenses the proper dose.

In operation, DPI devices strive to administer a uniform aerosol dispersion amount in a desired physical form of the dry powder (such as a particulate size) into a patient's airway and direct it to a desired deposit site(s). A number of obstacles can undesirably impact the performance of the DPI. For example, the small size of the inhalable particles in the dry powder drug mixture can subject them to forces of agglomeration and/or cohesion (certain types of dry powders are susceptible to agglomeration, which is typically caused by particles of the drug adhering together), which can result in poor flow and non-uniform dispersion. In addition, as noted above, many dry powder formulations employ larger excipient particles to promote flow properties of the drug. However, separation of the drug from the excipient, as well as the presence of agglomeration, can require additional inspiratory effort, which, again, can impact the stable dispersion of the powder within the air stream of the patient. Unstable dispersions may inhibit the drug from reaching its preferred deposit/destination site and can prematurely deposit undue amounts of the drug elsewhere.

Some inhalation devices have attempted to resolve problems attendant with conventional passive inhalers. For example, U.S. Pat. No. 5,655,523 proposes a dry powder inhalation device which has a deagglomeration/aerosolization plunger rod or biased hammer and solenoid, and U.S. Pat. No. 3,948,264 proposes the use of a battery-powered solenoid buzzer to vibrate the capsule to effectuate the release of the powder contained therein. These devices propose to facilitate the release of the dry powder by the use of energy input independent of patient respiratory effort. U.S. Pat. No. 6,029,663 to Eisele et al. proposes a dry powder inhaler delivery system with a rotatable carrier disk having a blister shell sealed by a shear layer that uses an actuator that tears away the shear layer to release the powder drug contents. The device also proposes a hanging mouthpiece cover that is attached to a bottom portion of the inhaler. U.S. Pat. No. 5,533,502 to Piper proposes a powder inhaler using patient inspiratory efforts for generating a respirable aerosol and also includes a rotatable cartridge holding the depressed wells or blisters defining the medicament holding receptacles. A spring-loaded carriage compresses the blister against conduits with sharp edges that puncture the blister to release the medication that is then entrained in air drawn in from the air inlet conduit so that aerosolized medication is emitted from the aerosol outlet conduit. The contents of all of these patents are hereby incorporated by reference as if stated in full herein.

Hickey et al., in U.S. Pat. No. 6,889,690 and PCT Patent Publication No. WO 01/68169A1 and related U.S. Pat. No. 6,971,383, have proposed a DPI system to actively facilitate the dispersion and release of dry powder drug formulations during inhalation using piezoelectric polymer film elements which may promote or increase the quantity of fine particle fraction particles dispersed or emitted from the device over conventional DPI systems. The contents of these documents are hereby incorporated by reference as if recited in full herein.

More recently, Eason et al., in U.S. Pat. No. 7,025,056 have proposed an inhaler for producing an inhalable aerosol of a powdered medicament that includes an aerosolizing device in the form of a vortex chamber.

Notwithstanding the above, there remains a need for alternative inhalers and/or airways that can be used with dry powder inhalers.

SUMMARY

Embodiments of the present invention provide dry powder inhalers that include a dry powder medicament container assembly, and a dry powder delivery tube that facilitates dry powder deagglomeration and that reduces the possibility of dry powder deposition therewithin. The delivery tube has an inlet that is configured to communicate with a dose container in the container assembly and an outlet at an opposite end. At least a portion of an inner wall of the tube has a substantially polygonal cross-section configuration. Dry powder medicament is drawn through the tube from a dose container in the container assembly upon user inhalation through the tube outlet.

In some embodiments, a dry powder inhaler includes a dry powder medicament container assembly, and an elongated dry powder delivery tube that facilitates dry powder deagglomeration and that reduces the possibility of dry powder deposition therewithin. The elongated delivery tube has an inlet at one end that is configured to communicate with a dose container in the container assembly, and an outlet or inhalation port that extends from the inhaler housing at an opposite end. The delivery tube also includes one or more apertures adjacent the inlet that supplement airflow into the delivery tube when a user inhales through the inhalation port. Other air inlet apertures may be provided in other locations, also. Dry powder medicament is drawn through the delivery tube from a dose container in the container assembly upon user inhalation through the inhalation port. The one or more apertures are oriented to cause a cyclonic or turbulent airflow through the delivery tube.

The inner surface of the delivery tube can have a polygonal configuration defined by a plurality of elongated planar surfaces oriented substantially parallel with a longitudinal axis of the delivery tube. Angles between adjacent elongated planar surfaces can be, for example, greater than or equal to about one-hundred five degrees (105°), greater than or equal to about one-hundred twenty degrees (120°), greater than or equal to about one-hundred thirty-five degrees (135°), etc. For example, the tube wall inner surface can have a hexagonal configuration with six (6) planar surfaces and wherein the angle between adjacent planar surfaces is one-hundred twenty degrees (120°). In some embodiments, substantially the entire tube wall inner surface can have a polygonal configuration.

The polygonal configuration of the tube wall inner surface causes the cyclonic air stream to bounce off the planar surfaces multiple times as the air stream flows through the delivery tube. The multiple impacts combined with the shear forces imparted by the cyclonic air stream facilitates deagglomeration of dry powder medicament entrained within the air stream. As such, the delivery tube serves as an effective deagglomeration chamber for deagglomerating dry powder medicament being inhaled therethrough by a user. The elongated configuration of the delivery tube can eliminate locations known as "dead zones" where dry powder can lose velocity and accumulate.

In other embodiments, a dry powder inhaler includes a dry powder medicament container assembly and first and second dry powder medicament conduits that facilitate deagglomeration of dry powder and that reduce the possibility of dry powder deposition therein. The first conduit has an arcuate configuration with an inlet that is configured to communicate with a dose container in the container assembly, an outlet, and an air inlet aperture that provides airflow into the first conduit. The arcuate configuration of the first conduit can reduce "dead zones" where dry powder can lose velocity and accumulate.

The second conduit can have a substantially straight configuration with a deagglomeration chamber at one end and an outlet at an opposite end that extends from the inhaler housing as an inhalation port. The first conduit outlet is in communication with the deagglomeration chamber of the second conduit. An inner surface of the deagglomeration chamber has a polygonal configuration with a plurality of elongated planar surfaces that are oriented substantially parallel with a longitudinal axis of the second conduit. Angles between adjacent elongated planar surfaces can be, for example, greater than or equal to about one-hundred five degrees (105°), greater than or equal to about one-hundred twenty degrees (120°), greater than or equal to about one-hundred thirty-five degrees (135°), etc. For example, the inner surface of the deagglomeration chamber can have a hexagonal configuration with six (6) planar surfaces and where the angle between adjacent planar surfaces is one-hundred twenty degrees (120°).

The air inlet aperture in the first conduit can provide additional or make-up airflow into the first conduit when a user inhales through the inhalation port. Inhalation by a user pulls the dry powder medicament from a dose container in communication with the first conduit inlet, with or without the assistance of additional or make-up air, and the dry powder medicament becomes entrained within the air stream. The air stream is directed into the deagglomeration chamber and impacts the polygonal inner surface of the deagglomeration chamber so as to facilitate deagglomeration of powdered medicament entrained therein. The arcuate configuration of the first conduit is particularly advantageous because powder particles can be efficiently directed into the deagglomeration chamber, for example, with a single bounce off of an internal surface of the first conduit. In addition, in some embodiments, the configuration of the first and second conduits can create a retrograde flow vector for an air stream entering the deagglomeration chamber. This can prolong the duration of the time the air stream, and dry powder entrained therein, resides within the deagglomeration chamber. This increased duration can be advantageous because of the greater number of impacts of powder particles on the inner surfaces of the deagglomeration chamber, which can result in a greater number of fine particles produced. In addition, the arcuate configuration of the first conduit can facilitate efficient incorporation thereof into an inhaler housing.

Various polygonal configurations are possible for the deagglomeration chamber inner surface including, but not limited to, heptagonal, octagonal, nonagonal, decagonal, etc., configurations. Embodiments of the present invention are not limited to tube wall inner surfaces with hexagonal configurations. The polygonal configuration of the deagglomeration chamber inner surface causes the air stream to bounce off of the planar surfaces multiple times as the air stream flows through the second conduit.

According to some embodiments of the present invention, operations for deagglomerating dry powder medicament in a dry powder inhaler include entraining dry powder medicament within an air stream, and then directing the air stream with dry powder entrained therein against a polygonal inner surface having a plurality of impact surfaces. In some embodiments, the air stream is a cyclonic or turbulent air stream.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

BRIEF DESCRIPTION OF THE DRAWINGS

FIG. 12 is a fragmentary perspective view of an inhaler utilizing the dose container assembly and first and second dry powder delivery conduits of FIG. 11.

FIG. 17 is a flow chart of exemplary operations for deagglomerating dry powder medicament in a dry powder inhaler according to some embodiments of the present invention.

DETAILED DESCRIPTION

Figure 1A:
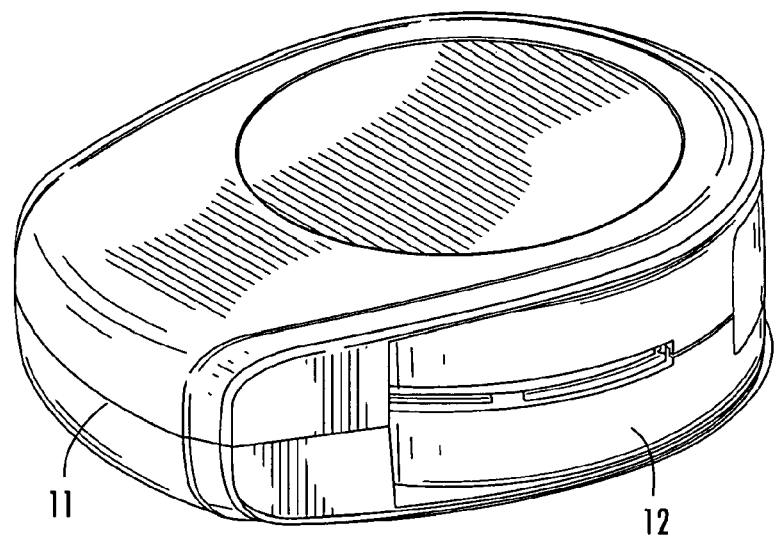
FIG. 1A is a front perspective view of an inhaler with a cover according to some embodiments of the present invention.

The present invention now is described more fully hereinafter with reference to the accompanying drawings, in which some embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

In the description of the present invention that follows, certain terms are employed to refer to the positional relationship of certain structures relative to other structures. As used herein, the term "front" or "forward" and derivatives thereof refer to the general or primary direction that dry powder travels to be dispensed to a patient from a dry powder inhaler; this term is intended to be synonymous with the term "downstream," which is often used in manufacturing or material flow environments to indicate that certain material traveling or being acted upon is farther along in that process than other material. Conversely, the terms "rearward" and "upstream" and derivatives thereof refer to the direction opposite, respectively, the forward or downstream direction.

The term "deagglomeration" and its derivatives refer to processing dry powder in the inhaler airflow path to inhibit the dry powder from remaining or becoming agglomerated or cohesive during inspiration.

The term "dead zone" refers to a localized area of low flow and/or pressure within a dry powder delivery tube/conduit of an inhaler.

The inhalers and methods of the present invention may be particularly suitable for holding a partial or bolus dose or doses of one or more types of particulate dry powder substances that are formulated for in vivo inhalant dispersion (using an inhaler) to subjects, including, but not limited to, animal and, typically, human subjects. The inhalers can be used for nasal and/or oral (mouth) respiratory inhalation delivery, but are typically oral inhalers. The terms "sealant", "sealant layer" and/or "sealant material" includes configurations that have at least one layer of at least one material; thus, such a phrase also includes multi-layer or multi-material sealant configurations. Thus, term "sealant layer" includes single and multiple layer materials, typically comprising a foil layer. The sealant layer can be a thin multi-layer laminated sealant material with elastomeric and foil materials. The sealant layer can be selected to provide drug stability as they may contact the dry powder in the respective dose containers.

The sealed dose containers can be configured to inhibit oxygen and moisture penetration to provide a sufficient shelf life.

The dry powder substance may include one or more active pharmaceutical constituents as well as biocompatible additives that form the desired formulation or blend. As used herein, the term "dry powder" is used interchangeably with "dry powder formulation" and means that the dry powder can comprise one or a plurality of constituents or ingredients with one or a plurality of (average) particulate size ranges. The term "low-density" dry powder means dry powders having a density of about 0.8 g/cm3 or less. In particular embodiments, the low-density powder may have a density of about 0.5 g/cm3 or less. The dry powder may be a dry powder with cohesive or agglomeration tendencies.

In any event, individual dispensable quantities of dry powder formulations can comprise a single ingredient or a plurality of ingredients, whether active or inactive. The inactive ingredients can include additives added to enhance flowability or to facilitate aerosolization delivery to the desired target. The dry powder drug formulations can include active particulate sizes that vary. The device may be particularly suitable for dry powder formulations having particulates which are in the range of between about 0.5-50 µm, typically in the range of between about 0.5 µm-20.0 µm, and more typically in the range of between about 0.5 µm-8.0 µm. The dry powder formulation can also include flow-enhancing ingredients, which typically have particulate sizes that may be larger than the active ingredient particulate sizes. In certain embodiments, the flow-enhancing ingredients can include excipients having particulate sizes on the order of about 50-100 µm. Examples of excipients include lactose and trehalose. Other types of excipients can also be employed, such as, but not limited to, sugars which are approved by the United States Food and Drug Administration ("FDA") as cryoprotectants (e.g., mannitol) or as solubility enhancers (e.g., cyclodextrine) or other generally recognized as safe ("GRAS") excipients.

"Active agent" or "active ingredient" as described herein includes an ingredient, agent, drug, compound, or composition of matter or mixture, which provides some pharmacologic, often beneficial, effect. This includes foods, food supplements, nutrients, drugs, vaccines, vitamins, and other beneficial agents. As used herein, the terms further include any physiologically or pharmacologically active substance that produces a localized and/or systemic effect in a patient.

The active ingredient or agent that can be delivered includes antibiotics, antiviral agents, anepileptics, analgesics, anti-inflammatory agents and bronchodilators, and may be inorganic and/or organic compounds, including, without limitation, drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system, and the central nervous system. Suitable agents may be selected from, for example and without limitation, polysaccharides, steroids, hypnotics and sedatives, psychic energizers, tranquilizers, anticonvulsants, muscle relaxants, anti-Parkinson agents, analgesics, anti-inflammatories, muscle contractants, antimicrobials, antimalarials, hormonal agents including contraceptives, sympathomimetics, polypeptides and/or proteins (capable of eliciting physiological effects), diuretics, lipid regulating agents, antiandrogenic agents, antiparasitics, neoplastics, antineoplastics, hypoglycemics, nutritional agents and supplements, growth supplements, fats, antienteritis agents, electrolytes, vaccines and diagnostic agents.

The active agents may be naturally occurring molecules or they may be recombinantly produced, or they may be analogs of the naturally occurring or recombinantly produced active agents with one or more amino acids added or deleted. Further, the active agent may comprise live attenuated or killed viruses suitable for use as vaccines. Where the active agent is insulin, the term "insulin" includes natural extracted human insulin, recombinantly produced human insulin, insulin extracted from bovine and/or porcine and/or other sources, recombinantly produced porcine, bovine or other suitable donor/extraction insulin and mixtures of any of the above. The insulin may be neat (that is, in its substantially purified form), but may also include excipients as commercially formulated. Also included in the term "insulin" are insulin analogs where one or more of the amino acids of the naturally occurring or recombinantly produced insulin has been deleted or added.

It is to be understood that more than one active ingredient or agent may be incorporated into the aerosolized active agent formulation and that the use of the term "agent" or "ingredient" in no way excludes the use of two or more such agents. Indeed, some embodiments of the present invention contemplate administering combination drugs that may be mixed in situ.

Examples of diseases, conditions or disorders that may be treated according to embodiments of the invention include, but are not limited to, asthma, COPD (chronic obstructive pulmonary disease), viral or bacterial infections, influenza, allergies, cystic fibrosis, and other respiratory ailments as well as diabetes and other insulin resistance disorders. The dry powder inhalation may be used to deliver locally-acting agents such as antimicrobials, protease inhibitors, and nucleic acids/oligonucleotides as well as systemic agents such as peptides like leuprolide and proteins such as insulin. For example, inhaler-based delivery of antimicrobial agents such as antitubercular compounds, proteins such as insulin for diabetes therapy or other insulin-resistance related disorders, peptides such as leuprolide acetate for treatment of prostate cancer and/or endometriosis and nucleic acids or oligonucleotides for cystic fibrosis gene therapy may be performed. See e.g., Wolff et al., Generation of Aerosolized Drugs, J. Aerosol. Med. pp. 89-106 (1994). See also U.S. Patent Application Publication No. 20010053761, entitled Method for Administering ASPB28-Human Insulin and U.S. Patent Application Publication No. 20010007853, entitled Method for Administering Monomeric Insulin Analogs, the contents of which are hereby incorporated by reference as if recited in full herein.

Typical dose amounts of the unitized dry powder mixture dispersed in the inhalers may vary depending on the patient size, the systemic target, and the particular drug(s). The dose amounts and type of drug held by a dose container system may vary per dose container or may be the same. In some embodiments, the dry powder dose amounts can be about 100 mg or less, typically less than 50 mg, and more typically between about 0.1 mg to about 30 mg.

In some embodiments, such as for pulmonary conditions (i.e., asthma or COPD), the dry powder can be provided as about 5 mg total weight (the dose amount may be blended to provide this weight). A conventional exemplary dry powder dose amount for an average adult is less than about 50 mg, typically between about 10-30 mg and for an average adolescent pediatric subject is typically from about 5-10 mg. A typical dose concentration may be between about 1-5%. Exemplary dry powder drugs include, but are not limited to, albuterol, fluticasone, beclamethasone, cromolyn, terbutaline, fenoterol, 8-agonists (including long-acting 8-agonists), salmeterol, formoterol, corticosteroids and glucocorticoids.

In certain embodiments, the administered bolus or dose can be formulated with an increase in concentration (an increased percentage of active constituents) over conventional blends. Further, the dry powder formulations may be configured as a smaller administrable dose compared to the conventional 10-25 mg doses. For example, each administrable dry powder dose may be on the order of less than about 60-70% of that of conventional doses. In certain particular embodiments, using the active dispersal systems provided by certain embodiments of the DPI configurations of the instant invention, the adult dose may be reduced to under about 15 mg, such as between about 10 μg-10 mg, and more typically between about 50 μg-10 mg. The active constituent(s) concentration may be between about 5-10%. In other embodiments, active constituent concentrations can be in the range of between about 10-20%, 20-25%, or even larger. In particular embodiments, such as for nasal inhalation, target dose amounts may be between about 12-100 μg.

In certain particular embodiments, during inhalation, the dry powder in a particular drug compartment or blister may be formulated in high concentrations of an active pharmaceutical constituent(s) substantially without additives (such as excipients). As used herein, "substantially without additives" means that the dry powder is in a substantially pure active formulation with only minimal amounts of other non-biopharmacological active ingredients. The term "minimal amounts" means that the non-active ingredients may be present, but are present in greatly reduced amounts, relative to the active ingredient(s), such that they comprise less than about 10%, and preferably less than about 5%, of the dispensed dry powder formulation, and, in certain embodiments, the non-active ingredients are present in only trace amounts.

In some embodiments, the unit dose amount of dry powder held in a respective dose container is less than about 10 mg, typically about 5 mg of blended drug and lactose or other additive (e.g., 5 mg LAC), for treating pulmonary conditions such as asthma. Insulin may be provided in quantities of about 4 mg or less, typically about 3.6 mg of pure insulin. The dry powder may be inserted into a dose container in a "compressed" or partially compressed manner or may be provided as free flowing particulates.

Some embodiments of the invention are directed to inhalers that can deliver multiple different drugs for combination delivery. Thus, for example, in some embodiments, some or all of the dose containers may include two different drugs or different dose containers may contain different drugs configured for dispensing substantially concurrently.

The inhalers can be configured to provide any suitable number of doses, typically between 30-120 doses, and more typically between about 30-60 doses. The inhalers can deliver one or a combination of drugs. In some embodiments, the inhalers can provide between about 30-60 doses of two different drugs (in the same or different unit amounts), for a total of between about 60-120 individual unit doses, respectively. The inhaler can provide between a 30 day to a 60 day (or even greater) supply of medicine. In some embodiments, the inhalers can be configured to hold about 60 doses of the same drug or drug combination, in the same or different unit amounts, which can be a 30 day supply (for a twice per day dosing) or a 60 day supply for single daily treatments.

Figure 1B:
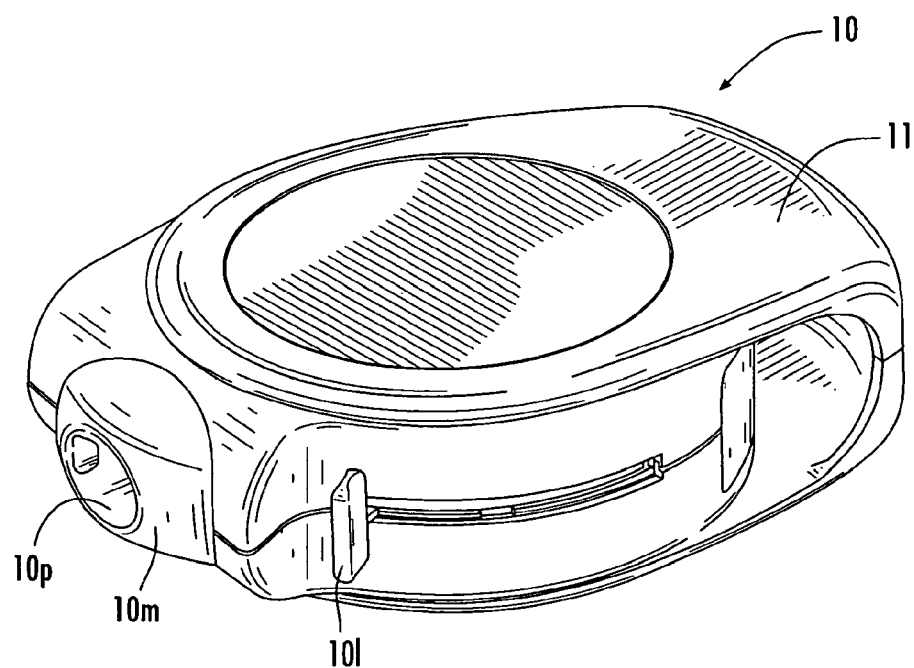
FIG. 1B is a front perspective of the inhaler shown in FIG. 1A with the cover in an open position according to some embodiments of the present invention.

Turning now to the figures, FIGS. 1A and 1B illustrate an example of a multi-dose inhaler 10 with a cover 11 and inhalation port 10p. The cover 11 may extend over a top surface of the inhaler to extend down over an inhalation port 10p of the mouthpiece 10m, then extend rearward away from the mouthpiece 10m over a bottom surface of the inhaler. However, this inhaler configuration is shown merely for completeness and embodiments of the invention are not limited to this inhaler configuration as other form factors, covers and inhalation port configurations may be used.

Figure 2A:
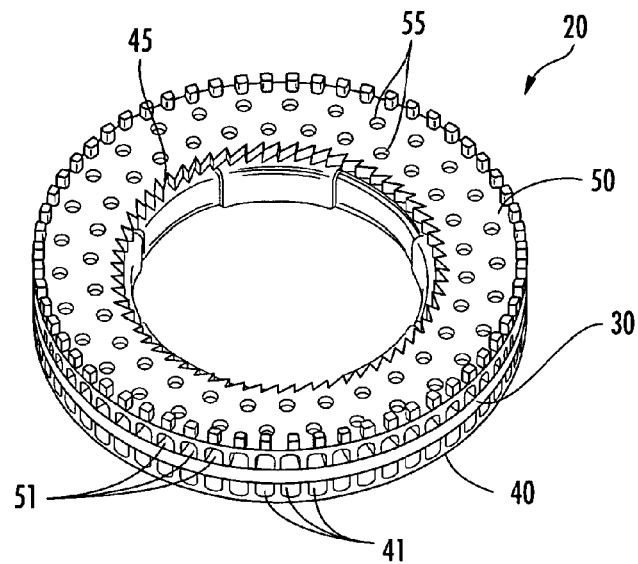
FIG. 2A is a top perspective view of an exemplary dose container assembly according to some embodiments of the present invention.
Figure 2B:
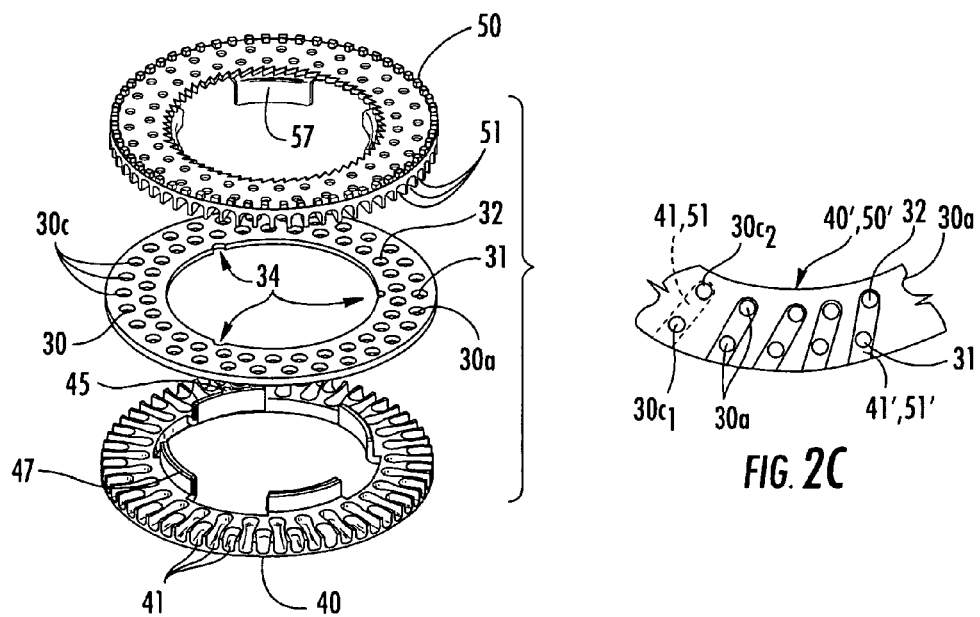
FIG. 2B is an exploded view of the assembly shown in FIG. 2A.
Figure 2C:
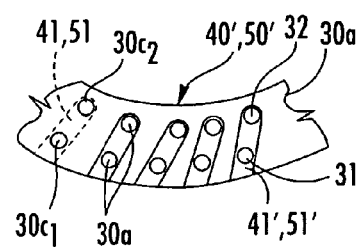
FIG. 2C is a partial cutaway view of airway channels aligned with two dose containers according to some embodiments of the present invention.

FIG. 2A illustrates a dose container assembly 20 with a dose ring or disk 30 having a plurality of dose containers 30c. As shown in FIGS. 2B and 2E, in some embodiments, the dose ring or disk 30 can include a plurality of circumferentially spaced apart through apertures 30a that form a portion of the dose containers 30c. As shown in FIG. 2E, the dose containers 30c can be defined by dose container apertures 30a and upper and lower sealants 36, 37.

As shown, the dose container assembly 20 includes a lower airway disk 40 and an upper airway disk 50. In other embodiments, the dose container assembly 20 can include the dose container disk 30 and only one of the lower airway disk 40 or the upper airway disk 50. In such a configuration, another type of airway can be used for the other side of the disk 30, such as, but not limited to, a fixed or "global" upper or lower airway can be used with the individual airways provided by either an upper or lower airway disk 50, 40. Also, it is contemplated that the upper and lower airway disks 50, 40 described herein can be reversed for normal operation (or inadvertently for atypical operation) so that the lower airway disk is the upper airway disk and the upper airway disk is the lower airway disk.

As shown in FIGS. 2A and 2B, the lower and upper airway disks 40, 50, respectively, include a plurality of circumferentially spaced apart airway channels 41, 51, respectively. Typically, the disks 40, 50 include one channel 41, 51 for one dose container 30c. However, in other embodiments, as shown, for example, in FIG. 2C, a respective airway channel 51, 41 from one or both of the disks 50', 40' can be in communication with two different dose containers 30c. This configuration will allow for (simultaneous) combination delivery of dry powder from two containers in a respective airway channel pair (or single) or can allow one dose container 30c₁ to release dry powder to the airway channel 41 and/or 51, then be used again later for the other dose container 30c₂. Thus, embodiments of the invention allow for some or all airway channels 41, 51 to be used once or twice (although other configurations may allow for greater number of uses). Also, while embodiments of the invention are illustrated as releasing only a dose from a single dose container 30c during one delivery, other embodiments allow the inhalers to dispense a combination drug so that two or more dose containers 30c may use a respective airway channel 41, 51 for delivery.

In some embodiments, the airway channels 41, 51 can define airways that are not able to release dry powder residing in a respective airway channel to a user once the inhaler is indexed again to another position so that the outer ring of dose containers are aligned with airway disks. The channels can be configured to have "sink traps" to inhibit spillage according to some embodiments of the present invention to provide overdose protection (unless the dual use configuration is used whereby only a single other dose may be released using that airway channel(s) as noted above).

Where two airway disks are used, e.g., both the lower and upper disks 40, 50, the inhaler device 10 can be configured to operate even when inverted and have the same overdose protection feature. Spillage of dry powder from the inhaler 10 as the dose container 30*c* is opened can be influenced by gravity. For example, for a conventional obround or elliptical mouthpiece shape, there are two primary device orientations (right-side-up and upside-down), embodiments of the invention allow for operation of the inhaler device in both orientations. In the embodiment shown, for example, in FIG. 2A, this can be accomplished by having an individual airway section for a respective dose container 30*c* (or dose containers where combination drug delivery is desired) both above and below the target corresponding dose container(s) 30*c*.

Figure 2D:
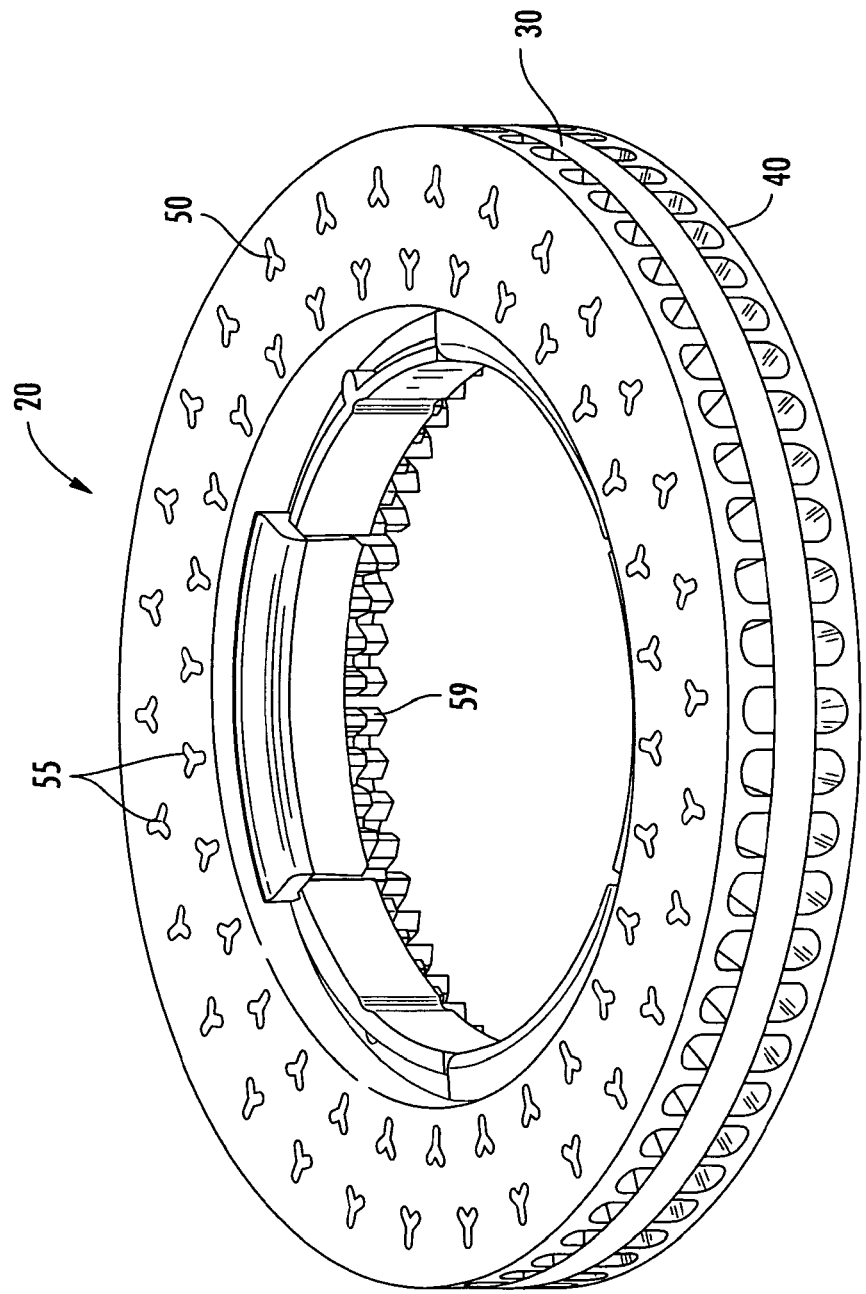
FIG. 2D is a top perspective view of another exemplary dose container assembly according to some embodiments of the present invention.
Figure 2E:
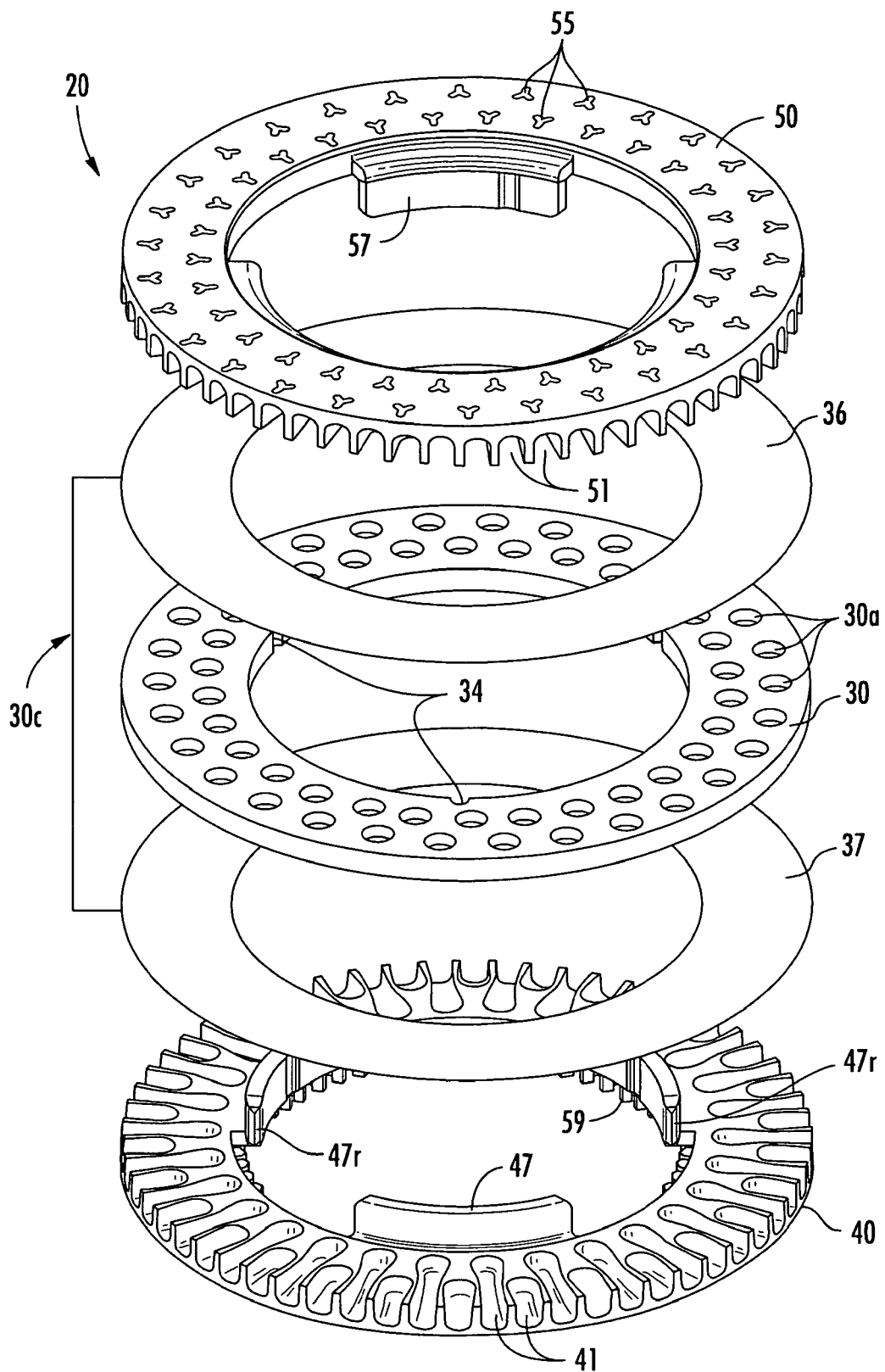
FIG. 2E is an exploded view of the dose container assembly shown in FIG. 2D according to embodiments of the present invention.
Figure 3A:
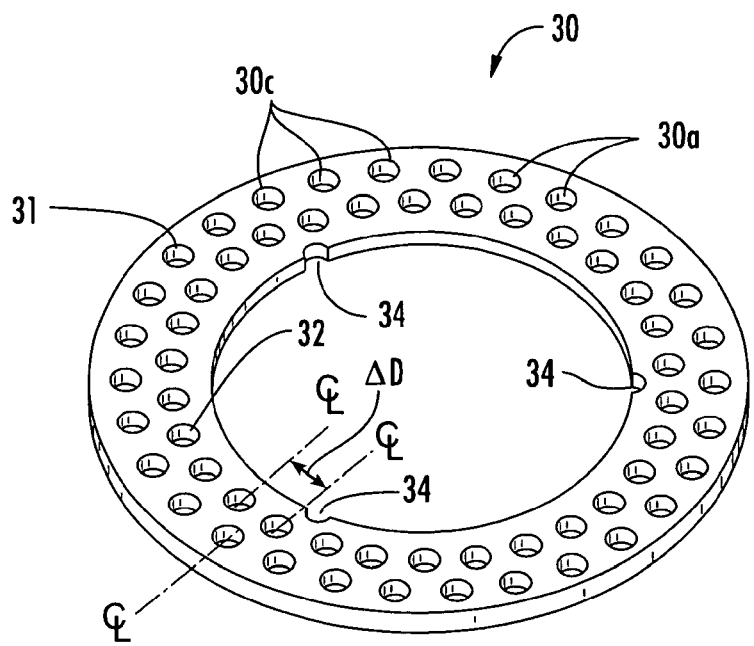
FIG. 3A is a top perspective view of a dose container ring according to some embodiments of the present invention.
Figure 3B:
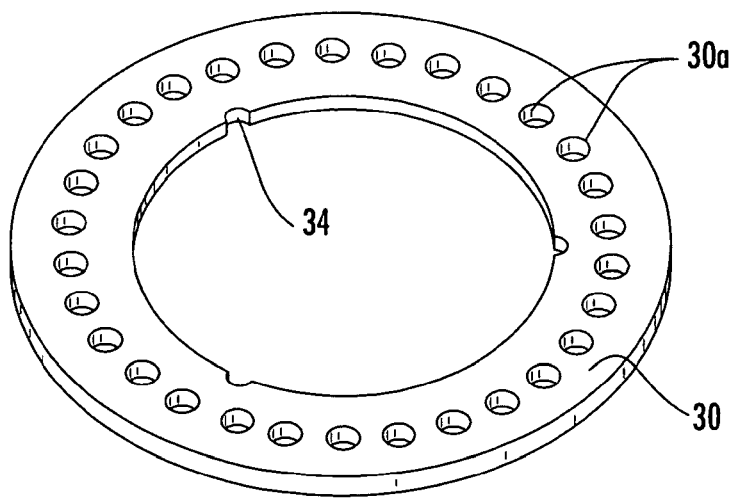
FIG. 3B is a top perspective view of a dose container ring according to some other embodiments of the present invention.

FIGS. 2A, 2D and 3A illustrate that the dose container disk 30 can include 60 dose containers 30*c* while FIG. 3B illustrates that the dose container disk 30 can include 30 dose containers 30*c*. Greater or lesser numbers of dose containers may be used.

FIG. 2E illustrates that sealant layers 36, 37 may be configured as annular flat rings as shown can be used to seal the top and bottom surfaces of the dose disk 30. The sealant layers 36, 37 can have the same or different material(s) and may include foil, polymer(s) and/or elastomer(s), or other suitable material or combinations of materials, including laminates. Typically, the sealant layers 36, 37 are thin flexible sealant layers comprising foil.

Figure 6:
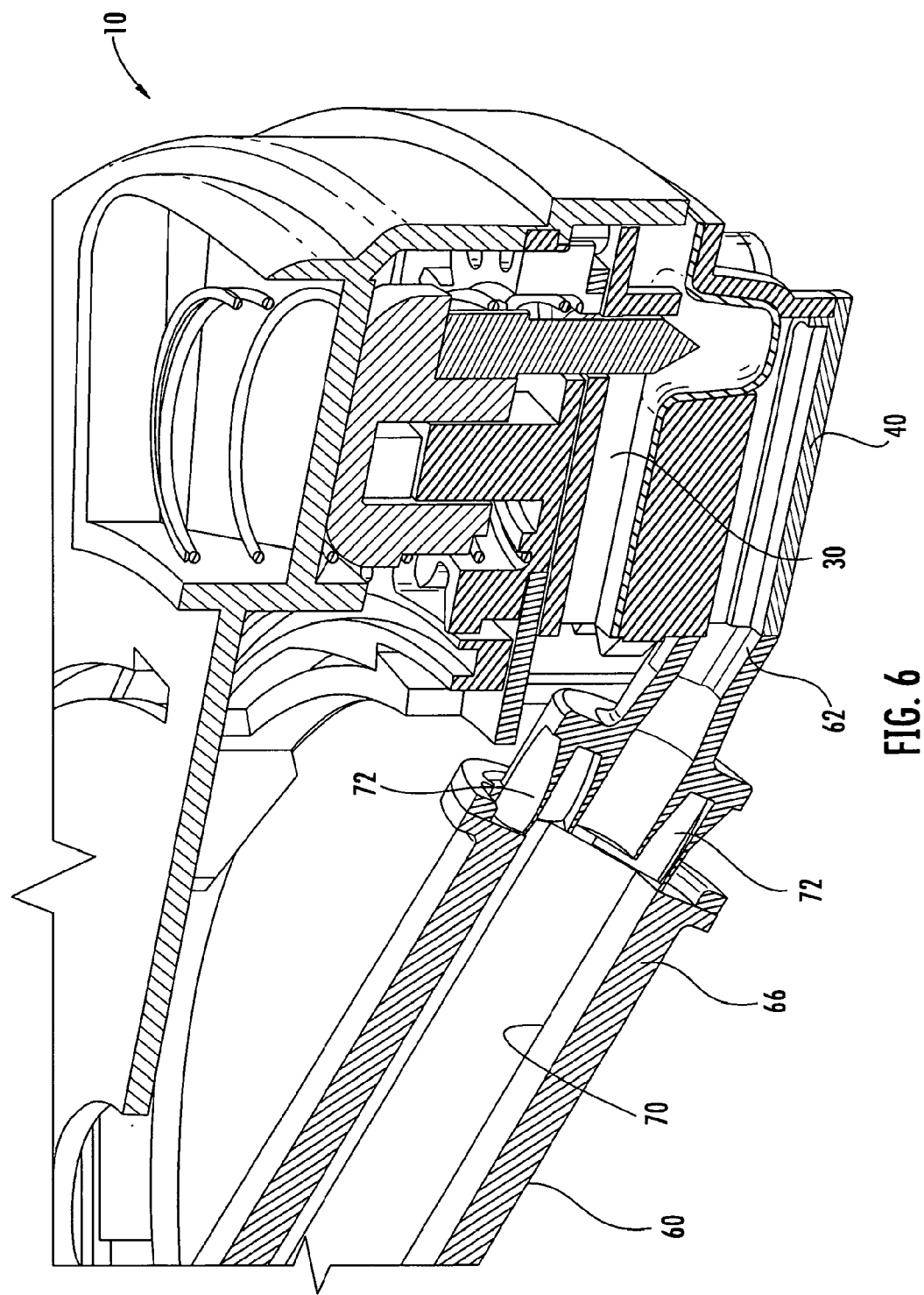
FIG. 6 is a fragmentary perspective view of an inhaler utilizing the dose container assembly and elongated delivery tube of FIG. 4.

The sealant layers 36, 37 (where used) may be provided as a substantially continuous ring as shown in FIG. 2E or may be attached to the dose container disk 30 as individual strips or spots of sealant that can be placed over and under the apertures 30*a*. In other embodiments, sealant layers may be provided on only one primary surface of the dose disk 30, and the apertures 30*a* may be closed on one side rather than have through apertures (not shown). In yet other embodiments, the dose disk 30 can have a blister configuration (FIG. 6).

FIGS. 2A, 2D, 3A and 3B also illustrate that the dose container disk 30 can include at least one indexing notch 34, shown as a plurality of circumferentially spaced apart indexing notches 34. A mating component on one of the other disks 40, 50 can be used to help orient the disks 30, 40, 50 relative to each other. For example, one of the airway disks 40, 50, typically the lower disk 40, may include an inner wall with an outwardly radially extending tab 45 (FIG. 2B) that aligns with and engages one of those notches 34 to position the channels 41, 51 in alignment with the dose containers 30*c*. Other alignment means may be used, including, for example, the reverse of the notch and tab configuration described (e.g., one or both airway disks 40, 50 can have a notch and the dose container disk 30 can include a tab or other component).

As shown in FIGS. 2B, 2D, 3A and 3B, the dose containers 30*c* may be arranged so that they are circumferentially spaced apart in one or more rows. As shown in FIG. 3A, the dose containers 30*c* are arranged in staggered concentric rows, a front row 31 at a first radius from a center of the disk and a back row 32 at a second different radius. The dose containers 30*c* can be arranged so that centerlines of the dose containers 30*c* of the back row are circumferentially offset from the centerlines of the dose containers 30*c* in the front row by a distance. As shown in FIG. 3A dose containers 30*c* on each respective row are spaced apart a distance "D" and the offset of the centerlines of those on the back row to those on the front row is "D/2". The dose container disk 30 can be a molded polymer, copolymer or blends and derivatives thereof, or may comprise metal, or combinations thereof, or other materials that are capable of providing sufficient moisture resistance.

The dose container disk 30 can have an outer diameter of between about 50-100 mm, typically about 65 mm and a thickness of between about 2-5 mm, typically about 3 mm. The disk 30 can comprise a cyclic olefin (COC) copolymer. The apertures 30*a* can have a diameter of between about 2-5 mm, typically about 3 mm and the sidewalls 30*w* of the dose containers 30*c* may have an angle or draft of about 1-3 degrees per side, typically about 1.5 degrees, as shown in FIG. 3D, to facilitate removal from a mold (where a molding process is used to form the disk 30). The dose container 30 is configured to be able to protect the powder from moisture ingress, while providing a desired number of doses in a compact overall inhaler size. The individual dose container apertures 30*a* are spaced apart from each other to allow sufficient seal area and material thickness for moisture protection of the powder.

Figure 3C:
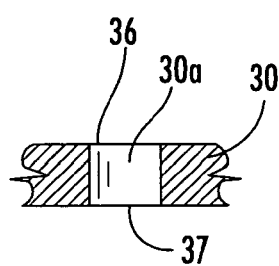
FIG. 3C is a partial cutaway view of a single dose container according to some embodiments of the present invention.
Figure 3D:
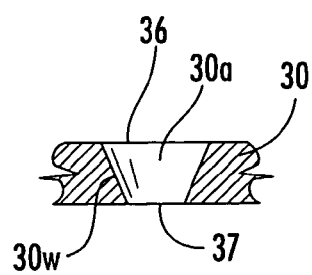
FIG. 3D is a partial cutaway view of a single dose container according to some embodiments of the present invention.

Similar to the embodiment shown in FIG. 2E, FIG. 3C illustrates that the dose containers 30*c* may be defined by apertures 30*a* sealed by sealant layers 36, 37 over and under the apertures 30*a*. As discussed above, the sealant layers 36, 37 can include foil, a polymer and/or elastomer, or other suitable materials or combinations of materials, including laminates. In a dry powder medicament inhaler 10, the drug powder is stored in a closed, moisture-resistant space provided by the dose containers 30*c*.

Embodiments of the invention provide a dose container assembly 20 that can provide a suitable seal and facilitate attachment of the airway disks 40, 50 to hold the dose ring or disk 30 therebetween. As shown in FIGS. 2D, 2E, in some embodiments, the dose container disk 30 contains sealants 36, 37 which may be a continuous layer over the upper and lower (primary) surfaces of the dose disk 30 and the upper and lower airway disks 50, 40 can contact the respective sealant and abut the dose disk 20 to allow for a tight fit. The exemplary attachment features shown in FIGS. 2A, 2E and 6 can reduce air leakage by allowing a close fit of the airway disks 40, 50 to the dose ring 30. The disks 40, 50 can sandwich the dose ring 30 and the dose ring can act as the "stop" to set the depth of engagement of the assembly features on the airway disks 40, 50. Embodiments of the invention provide a feature to index and/or orient the airway disks 40, 50 relative to the dose ring 30 as discussed above. In addition or alternatively, as shown in FIG. 2E, in some embodiments, relatively simple frictional engagement members, such as, but not limited to, "crush ribs" 47*r*, on one or both of the airway disks 40, 50 may be used to secure their attachment to each other as will be discussed further below.

Figure 4:
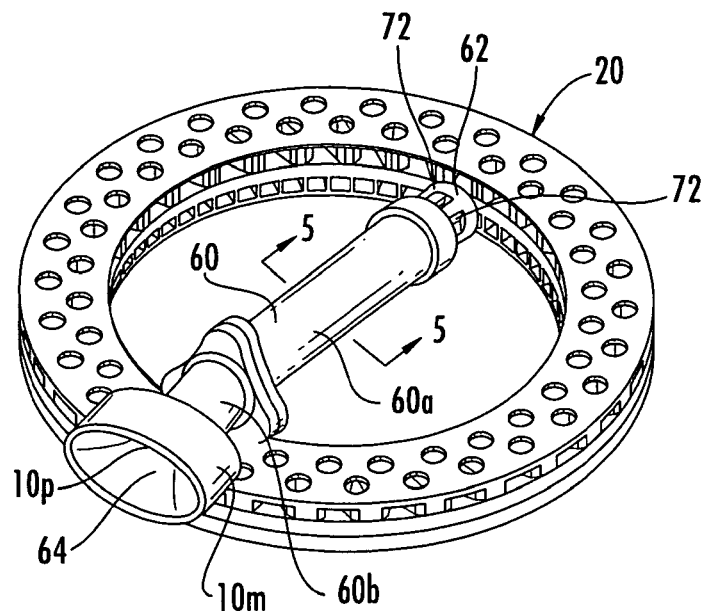
FIG. 4 is a top perspective view of a dry powder medicament container with an elongated dry powder delivery tube in communication therewith for use in dry powder inhalers, according to some embodiments of the present invention.

FIG. 4 illustrates a dry powder medicament container assembly 20 having an elongated dry powder delivery tube 60 for use with a dry powder inhaler, such as the inhaler 10 illustrated in FIGS. 1A-1B, according to some embodiments of the present invention. The illustrated delivery tube 60 has an inlet 62 at one end that is configured to communicate with a dose container 30*c* in the container assembly 20, and an outlet 64 at an opposite end that extends from housing 12 as inhalation port 10*p* in mouthpiece 10*m*. The outlet 64 may also merge into rather than include the mouthpiece 10*m*. The dose container assembly 20 is configured to be rotated within the housing 12 and the delivery tube inlet 62 is configured to align and communicate with a respective dose container 30*c*, for example, via one or both channels 41, 51.

The delivery tube 60 has a tube wall 66 (FIG. 5) that joins the inlet 62 and outlet 64. The delivery tube wall 66 has an outer surface 68 and an inner surface 70. In the illustrated embodiment, the outer surface 68 of the delivery tube wall 66 has a substantially cylindrical configuration. However, embodiments of the present invention are not limited to a delivery tube wall with a cylindrical configuration. Other configurations that facilitate assembly of the delivery tube 60 within an inhaler housing 12 can by utilized without limitation.

Figure 7:
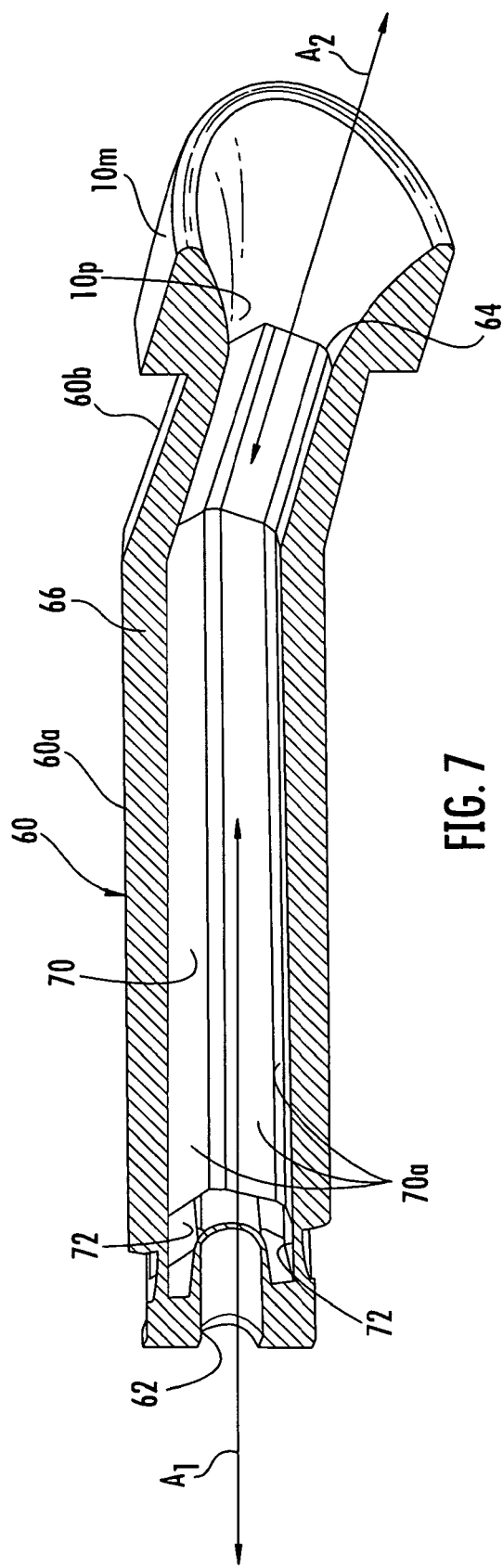
FIG. 7 is side section view of the elongated delivery tube of FIG. 4 illustrating the polygonal inner surface thereof.
Figure 8:
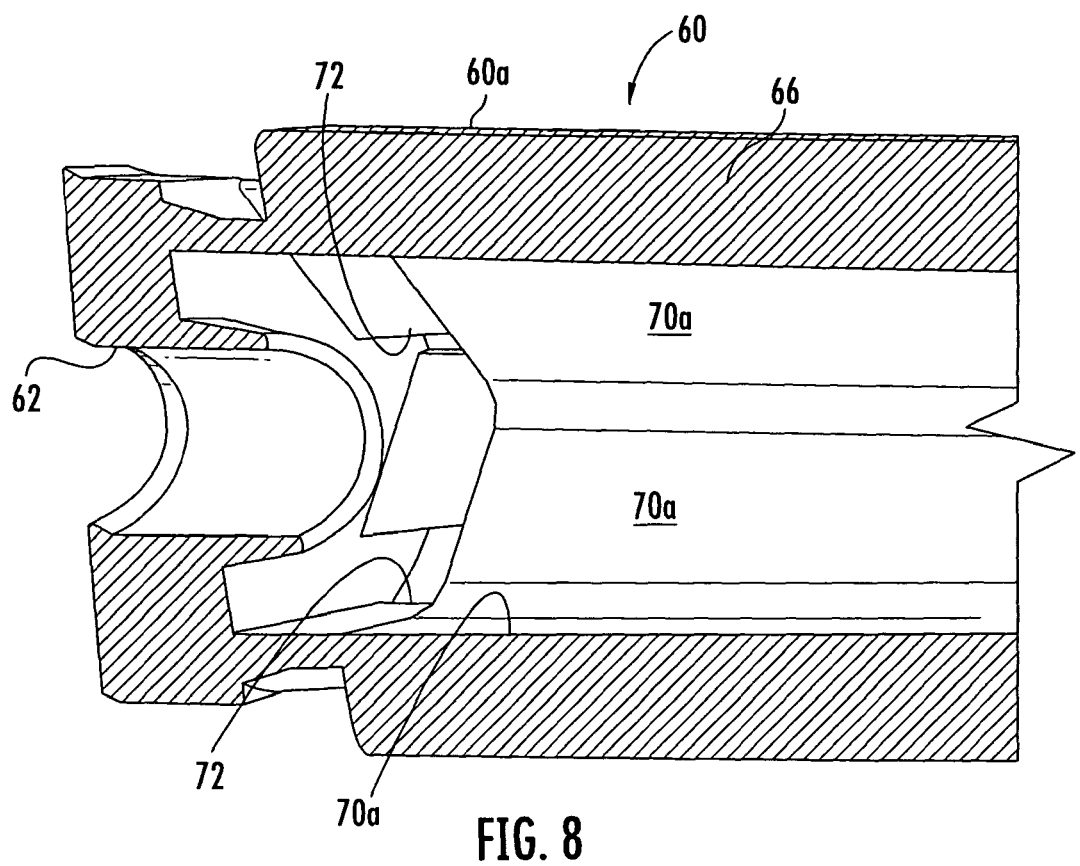
FIG. 8 is an enlarged partial section view of the inlet end of the elongated delivery tube of FIG. 7.
Figure 9:
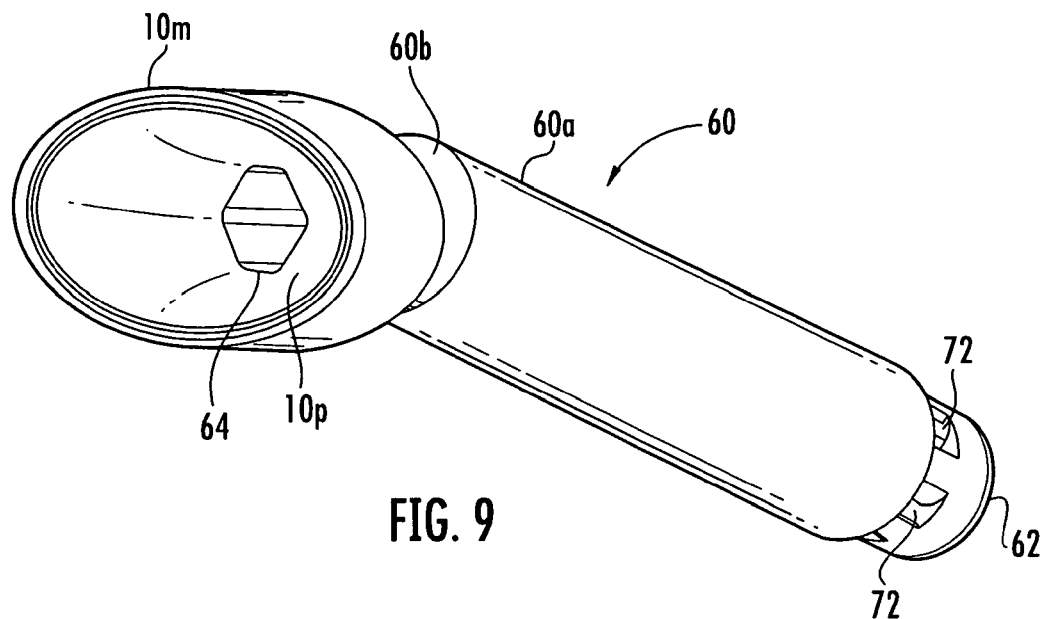
FIGS. 9-10 are perspectives views of the elongated delivery tube of FIG. 4.
Figure 10:
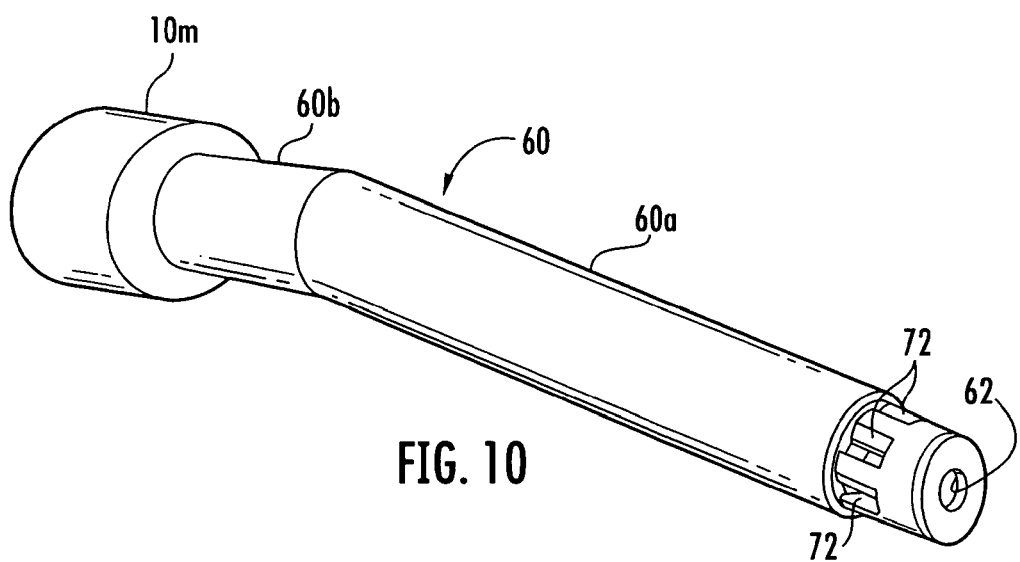

Referring to FIG. 7, in the illustrated embodiment, delivery tube 60 includes an elongated first portion 60a that defines a first axial direction $A_1$ and a shorter elongated second portion 60b that defines a second axial direction $A_2$. The illustrated configuration of first and second portions 60a, 60b can help accommodate the delivery tube 60 within the illustrated housing 12 of inhaler 10 (FIGS. 1A-1B). Moreover, the elongated configuration of the delivery tube first and second portions 60a, 60b can reduce the locations within the delivery tube 60 known as "dead zones" where dry powder can lose velocity and accumulate. However, embodiments of the present invention are not limited to the illustrated delivery tube 60 configuration. For example, delivery tube 60 can have a substantially straight configuration without any changes of direction (i.e., without portion 60b).

In some embodiments, bleed holes can be provided through the tube wall 66 in one or more locations to prevent dry powder deposition and/or to facilitate airflow through the delivery tube 60 during inhalation by a user.

Figure 5:
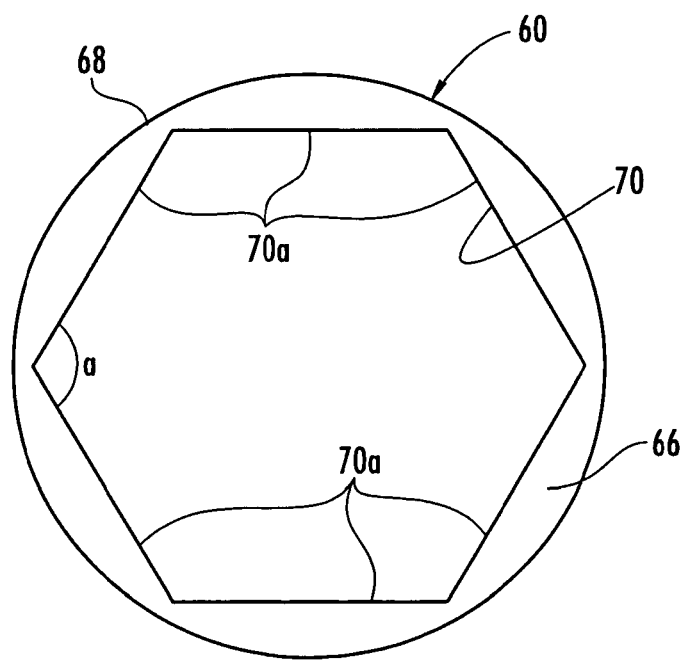
FIG. 5 is a cross-sectional view of the elongated delivery tube of FIG. 4, taken along lines 5-5 and illustrating the polygonal inner surface of the elongated delivery tube.

At least a portion of the tube wall inner surface 70 has a multi-facet configuration, e.g., a polygonal cross-section configuration with a plurality of elongated planar surfaces 70a that are oriented substantially parallel with a longitudinal axis $A_1$ of the delivery tube 60. For example, as illustrated in FIG. 5, the tube wall inner surface can have a hexagonal configuration with six (6) planar surfaces 70a. In some embodiments, substantially the entire tube wall inner surface 70 can have a polygonal configuration, as illustrated in FIG. 7. In the illustrated configuration of FIG. 7, both the first and second portions 60a, 60b have an inner surface with a polygonal configuration. The polygonal cross-section can transition to some other shape, for example at inlet 62 and/or outlet 64. In addition, the polygonal cross-section may flare out or have constant size along the distance/length of delivery tube 60.

Referring to FIGS. 7-10, the delivery tube wall 66 can include one or more apertures 72 adjacent the inlet 62 that provides airflow into the delivery tube 60 when a user inhales through the inhalation port 10p. This airflow supplements the airflow containing the dry powder medicament from a dose container 30c in communication with the tube inlet 62 and helps facilitate entrainment of the dry powder medicament within the air stream as would be understood by those skilled in the art of inhalers. In some embodiments, the apertures 72 are oriented such that airflow therethrough enters the tube 60 in a direction that is substantially transverse to a longitudinal axis $A_1$ of the tube such that the air stream impacts the tube wall inner surface 70.

In the illustrated embodiment, a plurality of circumferentially spaced-apart apertures 72 are provided. Apertures 72 can be configured as slots formed in the tube wall 66 that are oriented at acute radial angles to cause a turbulent or cyclonic air stream through the tube 60 when a user inhales through the inhalation port 10p. In some embodiments, the slots can be substantially tangential to the tube wall inner surface 70. The turbulent or cyclonic air stream with entrained dry powder from a dose container 30c repeatedly impacts the polygonal inner surface 70 of the delivery tube 60.

The polygonal configuration of the tube wall inner surface 70 causes the air stream to bounce off of each of the planar surfaces 70a (e.g., facets) numerous times as the air stream flows through the delivery tube 60. The multiple impacts combined with the shear forces imparted by the cyclonic air stream facilitates deagglomeration of dry powder medicament entrained within the air stream. As such, the delivery tube 60 serves as an effective deagglomeration chamber for deagglomerating dry powder medicament being inhaled therethrough by a user.

In some embodiments, the impact surfaces 70a may have a finish that facilitates deagglomeration. For example, the impact surfaces 70a may have a substantially smooth, polished finish that facilitates accurate particle bounce angles, such as a Society of the Plastics Industry (SPI) rated finish SPI A2. In other embodiments, the impact surfaces 70a may have a substantially rough or matte finish that facilitates particle spin, such as an SPI B3 finish.

Air inlet apertures 72 can have various configurations for generating cyclonic air streams, and embodiments of the present invention are not limited to the illustrated number or configuration of apertures 72. In addition, various polygonal configurations are possible for the delivery tube inner surface 70 including, but not limited to, heptagonal, octagonal, nonagonal, decagonal, etc., configurations. Embodiments of the present invention are not limited to tube wall inner surfaces with hexagonal configurations. Angles between adjacent elongated planar surfaces 70a can be, for example, greater than or equal to about one-hundred five degrees (105°), greater than or equal to about one-hundred twenty degrees (120°), greater than or equal to about one-hundred thirty-five degrees (135°), etc.

Referring to FIGS. 7-10, the delivery tube inlet 62 can be smaller than the delivery tube outlet 64. For example, a cross-sectional area of the tube inlet 62 can be less than or equal to a cross-sectional area of the tube outlet 64. An air stream flowing though the delivery tube 60 creates a low pressure core that helps pull air through a dose container to remove powder therefrom. In addition, Applicants have discovered that a delivery tube outlet 64 that is larger than the delivery tube inlet 62 also facilitates evacuation of dose containers 30c.

Figure 11:
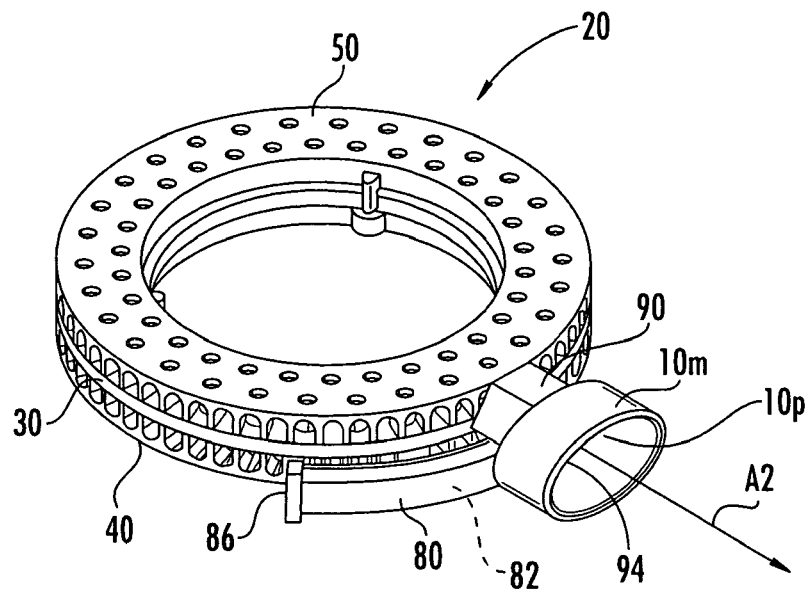
FIG. 11 is a top perspective view of a dry powder medicament container with first and second dry powder delivery conduits in communication therewith for use in dry powder inhalers, according to some embodiments of the present invention.

FIG. 11 illustrates a dry powder medicament container assembly 20 and first and second dry powder medicament conduits 80, 90 for use with a dry powder inhaler, such as the inhaler 10 illustrated in FIGS. 1A-1B, according to some embodiments of the present invention. The first conduit 80 has an arcuate configuration with an inlet 82 that is configured to communicate with a dose container 30c in the container assembly 20, an outlet 84, and an air inlet aperture 86 that provides airflow into the first conduit 80 (FIG. 12). The container assembly 20 is configured to be rotated within the housing 12 and the first conduit inlet 82 is configured to align and communicate with at least one dose container 30c in an indexed and/or dispensing position.

The arcuate configuration of the first conduit 80 facilitates assembly within the housing 12 of the inhaler 10 (FIGS. 1A-1B). The arcuate configuration of the first conduit 80 can also reduce locations within the first conduit 80 known as "dead zones" where dry powder can lose velocity and accumulate. In some embodiments, the arcuate configuration can be more pronounced between the inlet 82 and outlet 84 to further reduce the possibility of dry powder deposition between the inlet 82 and outlet 84. This is illustrated in FIGS. 13-16. The portion 83 of the first conduit 80 between the inlet 82 and the outlet 84 has a more pronounced arcuate configuration than the first conduit 80 of FIG. 11. In some embodiments, bleed holes can be provided in the first conduit 80 in one or more locations to prevent dry powder deposition. For example, a bleed hole can be provided in the arcuate portion 83.

Figure 15:
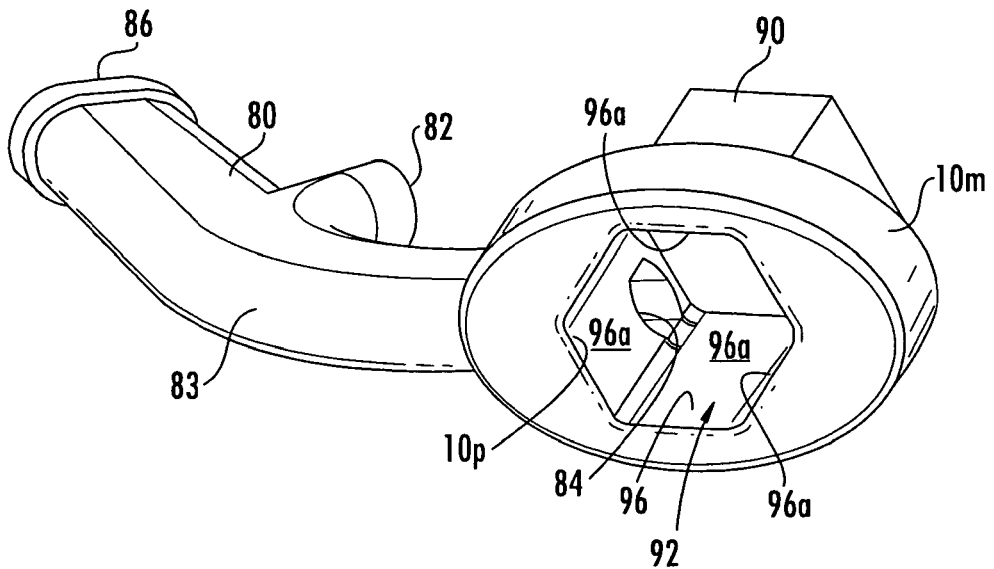
FIGS. 15-16 are front and rear perspectives views, respectively, of the first and second dry powder delivery conduits of FIG. 13.
Figure 16:
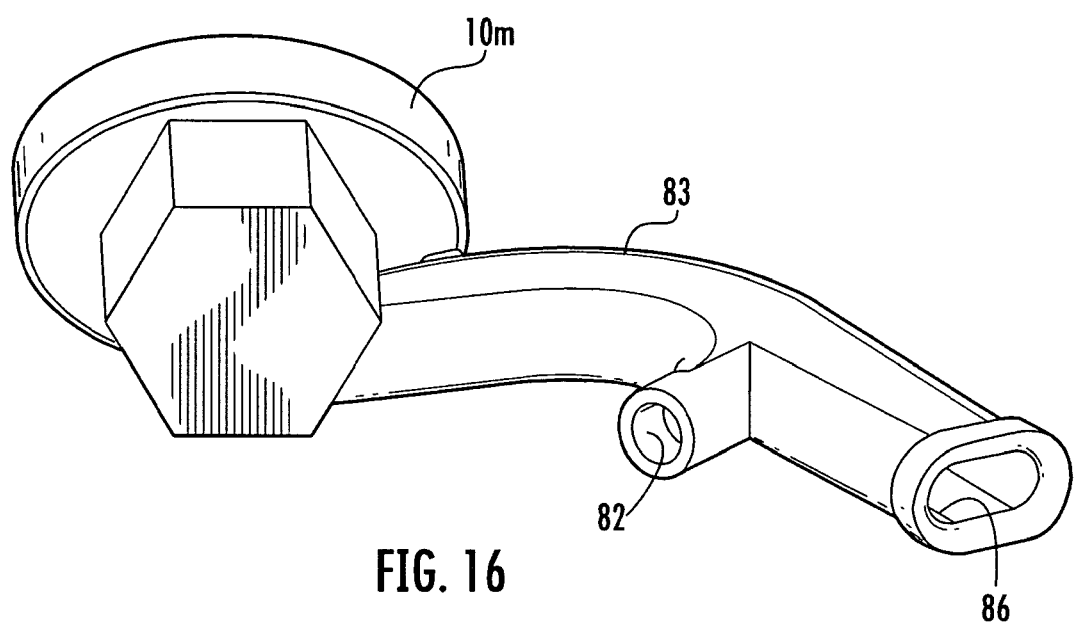

The second conduit 90 has a substantially straight configuration with a deagglomeration chamber 92 that merges into an outlet 94 that extends from housing 12 as inhalation port 10*p* in mouthpiece 10*m*. The first conduit outlet 84 is in communication with the deagglomeration chamber 92 of the second conduit 90. An inner surface 96 of the deagglomeration chamber 92 has a polygonal configuration with a plurality of elongated planar surfaces 96*a* (FIG. 15) that are oriented substantially parallel with a longitudinal axis $A_2$ of the second conduit 90. For example, as illustrated in FIG. 15, the inner surface 96 of the deagglomeration chamber 92 can have a hexagonal configuration with six (6) planar surfaces 96*a*.

User inhalation via inhalation port 10*p* pulls the dry powder medicament from a dose container 30*c* in communication with the first conduit inlet 82 and the dry powder medicament becomes entrained within the air stream as would be understood by those skilled in the art of inhalers. The air inlet aperture 86 in the first conduit provides additional or make-up airflow into the first conduit 80 when a user inhales through the inhalation port 10*p*. However, air inlet aperture 86 may not be needed. In some embodiments, the clearance between the first conduit inlet 82 and an airway disk channel 41, 51 may provide sufficient makeup air therethrough.

The air stream is directed into the deagglomeration chamber 92 where the air stream and dry powder entrained therein impacts the polygonal inner surface 96 of the deagglomeration chamber 92 so as to facilitate deagglomeration of powdered medicament entrained therein. The air inlet aperture 86 may be located virtually anywhere in the first conduit, and embodiments of the present invention are not limited to the illustrated location of air inlet aperture 86.

The curved configuration of the first conduit 80 facilitates efficient entry of the air stream and powder entrained therein into the deagglomeration chamber 92. The first conduit inlet is oriented such that larger dry powder particles entering through the first conduit inlet 82 bounce off of the inner surface of the first conduit 80 at an angle that directs the larger dry powder particles substantially directly into the deagglomeration chamber 92. As such, only a single bounce of the larger dry powder particles off of the inner surface of the first conduit 80 may occur. Smaller dry powder particles are of sufficiently small mass to pass through the bend 83 without impacting the wall (i.e., the inner surface of the first conduit 80).

Figure 13:
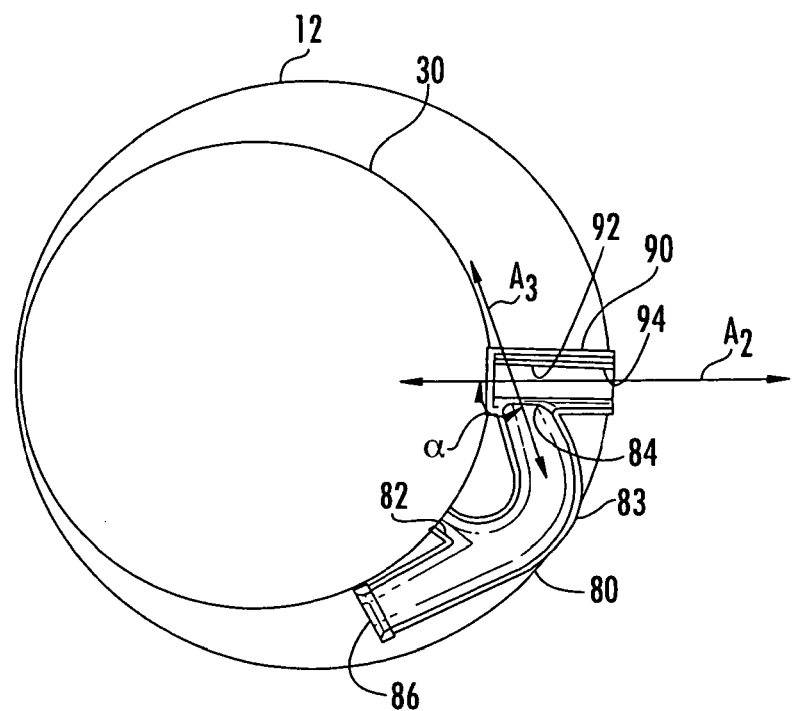
FIG. 13 is a top section view of a dry powder inhaler with first and second dry powder delivery conduits, according to other embodiments of the present invention.
Figure 14:
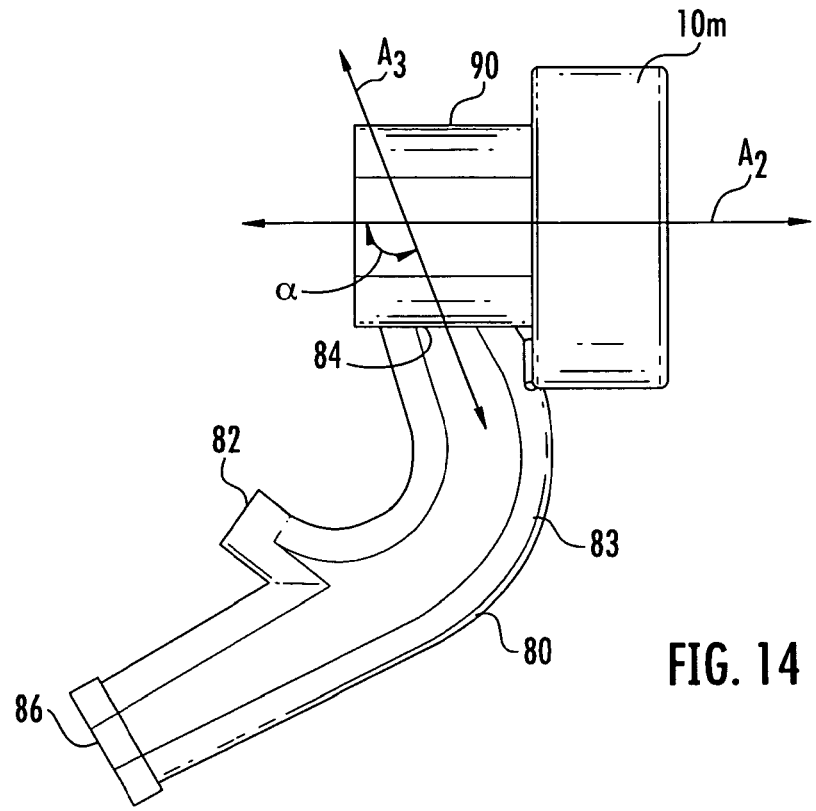
FIG. 14 is a top plan view of the first and second dry powder delivery conduits of FIG. 13.

In some embodiments, the first conduit outlet 84 is oriented such that airflow therethrough enters the deagglomeration chamber 92 in a direction that is substantially transverse to a longitudinal axis $A_2$ of the second conduit such that the air stream impacts the deagglomeration chamber inner surface 96 substantially orthogonally. In some embodiments, the first conduit outlet 84 is in communication with the deagglomeration chamber 92 such that airflow entering the deagglomeration chamber 92 from the first conduit outlet 84 is directed along a direction that extends away from the second conduit outlet 94 (inhalation port 10*p*). This is illustrated in FIG. 13, wherein the first conduit outlet defines an axial direction $A_3$ that is transverse to the axial direction $A_2$ of the second conduit and wherein $A_3$ extends away from the inhalation port 10*p*. In other words, the first conduit outlet 84 is in communication with the deagglomeration chamber 92 such that airflow entering the deagglomeration chamber 92 from the first conduit outlet 84 is directed along a direction that defines an obtuse angle α relative to an axial direction $A_2$ of the second conduit outlet 94. The first conduit 80 may be oriented relative to the second conduit 90 such that axial direction $A_3$ may have various transverse angles to the second conduit axial direction $A_2$, without limitation. As such, in the embodiment illustrated in FIG. 13, an air stream with dry powder entrained therein enters the deagglomeration chamber 92 with a retrograde flow vector (i.e., a direction component that extends away from the inhalation port 10*p*), which can prolong the duration of the time the air stream, and dry powder entrained therein, resides within the deagglomeration chamber 92. Prolonged duration in the deagglomeration chamber 92 can increase the number of powder particle impacts and can increase the number of fine particles produced.

The polygonal configuration of the deagglomeration chamber inner surface 96 causes the air stream to bounce off of the planar surfaces 96*a* multiple times as the air stream flows through the second conduit 90, thereby facilitating deagglomeration of the dry powder medicament entrained within the air stream. In some embodiments, the impact surfaces 96*a* may have a finish that facilitates deagglomeration. For example, the impact surfaces 96*a* may have a substantially smooth, polished finish that facilitates accurate particle bounce angles, such as an SPI A2 finish. In other embodiments, the impact surfaces 96*a* may have a substantially rough or matte finish that facilitates particle spin, such as an SPI B3 finish.

Various polygonal configurations are possible for the deagglomeration chamber inner surface 96 including, but not limited to, heptagonal, octagonal, nonagonal, decagonal, etc., configurations. Embodiments of the present invention are not limited to tube wall inner surfaces with hexagonal configurations. Angles between adjacent elongated planar surfaces 96*a* can be, for example, greater than or equal to about one-hundred five degrees (105°), greater than or equal to about one-hundred twenty degrees (120°), greater than or equal to about one-hundred thirty-five degrees (135°), etc.

FIG. 17 illustrates exemplary operations for deagglomerating dry powder medicament in a dry powder inhaler 10 according to some embodiments of the present invention. Dry powder medicament is entrained within an air stream (Block 100), for example, by a user inhaling through inhalation port 10*p* of inhaler 10. The air stream may be a cyclonic or otherwise turbulent air stream. The air stream with dry powder entrained therein is directed against a polygonal inner surface of a delivery conduit/tube, resulting in multiple impacts and swirling airflow (Block 110). This facilitates deagglomeration of the dry powder without causing the dry powder to lose velocity and accumulate within the inhaler.

The dose container assembly and inhaler embodiments described herein may be particularly suitable for dispensing medicament for the treatment of respiratory disorders. Appropriate medicaments may be selected from, for example, analgesics, e.g., codeine, dihydromorphine, ergotamine, fentanyl or morphine; anginal preparations, e.g., diltiazem; antiallergics, e.g., cromoglycate, ketotifen or nedocromil; antiinfectives e.g., cephalosporins, penicillins, streptomycin, sulphonamides, tetracyclines and pentamidine; antihistamines, e.g., methapyrilene; anti-inflammatories, e.g., beclomethasone dipropionate, fluticasone propionate, flunisolide, budesonide, rofleponide, mometasone furoate or triamcinolone acetonide; antitussives, e.g., noscapine; bronchodilators, e.g., albuterol, salmeterol, ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol, or (−)-4-amino-3,5-dichloro-α-[[6-[2-(2-pyridinyl) ethoxy] hexyl] methyl] benzenemethanol; diuretics, e.g., amiloride; anticholinergics, e.g., ipratropium, tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon. It will be clear to a person of skill in the art that, where appropriate, the medicaments may be used in the form of salts, (e.g., as alkali metal or amine salts or as acid addition salts) or as esters (e.g., lower alkyl esters) or as solvates (e.g., hydrates) to optimize the activity and/or stability of the medicament.

Some particular embodiments of the dose container assembly and/or inhaler described herein include medicaments that are selected from the group consisting of: albuterol, salmeterol, fluticasone propionate and beclometasone dipropionate and salts or solvates thereof, e.g., the sulphate of albuterol and the xinafoate of salmeterol.

Medicaments can also be delivered in combinations. Examples of particular formulations containing combinations of active ingredients include those that contain salbutamol (e.g., as the free base or the sulphate salt) or salmeterol (e.g., as the xinafoate salt) in combination with an anti-inflammatory steroid such as a beclomethasone ester (e.g., the dipropionate) or a fluticasone ester (e.g., the propionate).

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A dry powder inhaler, comprising:
a dry powder container assembly; and
an elongated dry powder delivery tube having a first end with an inlet that has an orientation defined by a first central longitudinal axis and that is configured to communicate with a dose container in the container assembly, a second end that is opposite the first end and that has an outlet that has an orientation defined by a second central longitudinal axis, and a tube wall having a portion with substantially cylindrical outer surface, and wherein at least a longitudinally extending portion of an inner surface of the tube wall has a substantially polygonal cross-section configuration, wherein a plurality of circumferentially spaced-apart air inlet apertures are formed through the tube wall portion adjacent the delivery tube inlet to provide airflow into the tube, and wherein the plurality of air inlet apertures are oriented such that airflow therethrough enters the tube in a direction that is substantially transverse to a longitudinal axis of the tube;
wherein dry powder is drawn through the tube from a dose container in the container assembly upon user inhalation through the tube outlet, and wherein the orientation of the first central longitudinal axis relative to the second central longitudinal axis defines an obtuse angle therebetween.

2. The inhaler of claim 1, wherein the at least one air inlet aperture is oriented to cause airflow through the tube to impact the portion of the tube wall inner surface having the polygonal configuration so as to facilitate deagglomeration of dry powder entrained therein.

3. The inhaler of claim 1, wherein the tube outlet comprises an inhalation port.

4. The inhaler of claim 1, wherein a cross-sectional area of the delivery tube inlet is less than or equal to a cross-sectional area of the delivery tube outlet.

5. The inhaler of claim 1, wherein the polygonal cross-section is hexagonal.

6. The inhaler of claim 1, wherein the portion of the tube wall inner surface having the polygonal configuration comprises a plurality of elongated planar surfaces oriented substantially parallel with a longitudinal axis of the tube, and wherein an angle between adjacent elongated planar surfaces is greater than or equal to about one-hundred five degrees (105°).

7. The inhaler of claim 1, wherein the portion of the tube wall inner surface having the polygonal configuration comprises a plurality of elongated planar surfaces oriented substantially parallel with a longitudinal axis of the tube, and wherein an angle between adjacent elongated planar surfaces is greater than or equal to about one-hundred twenty degrees (120°).

8. The inhaler of claim 1, wherein the portion of the tube wall inner surface having the polygonal configuration comprises a plurality of elongated planar surfaces oriented substantially parallel with a longitudinal axis of the tube, and wherein an angle between adjacent elongated planar surfaces is greater than or equal to about one-hundred thirty-five degrees (135°).

9. The inhaler of claim 1, wherein the portion of the tube wall inner surface having the polygonal configuration extends greater than ten millimeters (10 mm).

10. A dry powder inhaler, comprising:
a dry powder container assembly; and
a dry powder delivery tube, wherein the dry powder delivery tube comprises:
a first conduit having an inlet configured to communicate with a dose container in the container assembly, and an outlet, wherein the first conduit has an arcuate configuration; and
a second conduit having a deagglomeration chamber and an outlet, wherein the deagglomeration chamber has a polygonal cross-section, and wherein the first conduit outlet is in communication with the deagglomeration chamber such that airflow entering the deagglomeration chamber from the first conduit outlet is directed along a direction that extends away from the second conduit outlet and defines an obtuse angle relative to an axial direction of the second conduit outlet;
wherein dry powder is drawn from a dose container in the dry powder container assembly and through the first and second conduits upon user inhalation through the second conduit outlet.

11. The inhaler of claim 10, wherein the first conduit outlet defines an axial direction that is substantially transverse to an axial direction of the second conduit.

12. The inhaler of claim 10, wherein the first conduit outlet is in communication with the second conduit deagglomeration chamber such that airflow into the deagglomeration chamber impacts the polygonal inner surface so as to facilitate deagglomeration of dry powder entrained therein.

13. The inhaler of claim 10, wherein the second conduit outlet has a substantially straight configuration.

14. The inhaler of claim 10, wherein the first conduit has an arcuate configuration such that large dry powder particles from the first conduit inlet impact an inner surface of the first conduit and are reflected directly into the second conduit.

15. A method of deagglomerating dry powder in a dry powder inhaler, comprising:
entraining dry powder within an air stream; and
impacting the air stream against a polygonal inner surface of a conduit to thereby facilitate deagglomeration of the dry powder, wherein the conduit includes an outlet, and wherein the air stream enters the conduit in a direction that extends away from the conduit outlet and defines an obtuse angle relative to an axial direction of the conduit outlet;

wherein the polygonal inner surface comprises a plurality of elongated planar surfaces oriented substantially parallel with a longitudinal axis of the conduit, and wherein an angle between adjacent elongated planar surfaces is greater than or equal to about one-hundred five degrees (105°), greater than or equal to about one-hundred twenty degrees (120°), or greater than or equal to about one-hundred thirty-five degrees (135°).

* * * * *